United States Patent
Uger et al.

(10) Patent No.: US 9,296,819 B2
(45) Date of Patent: Mar. 29, 2016

(54) ANTIBODIES AND CONJUGATES THAT TARGET MISFOLDED PRION PROTEIN

(71) Applicants: ProMIS Neurosciences Inc., Toronto (CA); Helix BioPharma Corp., Aurora (CA)

(72) Inventors: Marni Diane Uger, Richmond Hill (CA); Viengthong Chai, Brampton (CA); Veronica Ciolfi, Brampton (CA); Neil R. Cashman, Vancouver (CA); Baomin Tian, Edmonton (CA); Wah Yau Wong, Edmonton (CA); Heman Lap-Man Chao, Aurora (CA)

(73) Assignees: ProMIS Neurosciences Inc., Toronto, ON (CA); Helix BioPharma Corp., Aurora, ON (CA)

( * ) Notice: Subject to any disclaimer, the term of this patent is extended or adjusted under 35 U.S.C. 154(b) by 0 days.

(21) Appl. No.: 14/407,724

(22) PCT Filed: Jun. 11, 2013

(86) PCT No.: PCT/CA2013/000569
§ 371 (c)(1),
(2) Date: Dec. 12, 2014

(87) PCT Pub. No.: WO2013/185215
PCT Pub. Date: Dec. 19, 2013

(65) Prior Publication Data
US 2015/0166668 A1 Jun. 18, 2015

Related U.S. Application Data

(60) Provisional application No. 61/658,569, filed on Jun. 12, 2012, provisional application No. 61/809,604, filed on Apr. 8, 2013.

(51) Int. Cl.
| | |
|---|---|
| *C07K 16/18* | (2006.01) |
| *G01N 33/53* | (2006.01) |
| *A61K 39/395* | (2006.01) |
| *A61K 47/48* | (2006.01) |
| *A61K 31/337* | (2006.01) |
| *G01N 33/68* | (2006.01) |
| *C07K 16/28* | (2006.01) |
| *A61K 38/50* | (2006.01) |

(52) U.S. Cl.
CPC ............ *C07K 16/2872* (2013.01); *A61K 31/337* (2013.01); *A61K 38/50* (2013.01); *A61K 39/3955* (2013.01); *A61K 47/4843* (2013.01); *A61K 47/48538* (2013.01); *A61K 47/48561* (2013.01); *G01N 33/6872* (2013.01); *G01N 33/6896* (2013.01); *C07K 2317/34* (2013.01); *C07K 2317/92* (2013.01); *C12Y 305/01005* (2013.01); *G01N 2333/70596* (2013.01); *G01N 2800/2828* (2013.01)

(58) Field of Classification Search
CPC ............ C07K 16/2872; A61K 39/3955; A61K 47/48538; A61K 47/4843; A61K 47/48638; A61K 47/4863; A61K 31/337
See application file for complete search history.

(56) References Cited

U.S. PATENT DOCUMENTS

2003/0148374 A1* 8/2003 Kurano et al. ......... C07K 16/18
435/7.1

FOREIGN PATENT DOCUMENTS

WO 2010/040209 A1 4/2010

OTHER PUBLICATIONS

Uger, Marni D. et al., Abstract 4636: AMF-1c-120: an antibody specific for misfolded expressed on ovarian cancer cells. Cancer Research Apr. 15, 2013, 73;4636.
Uger, Marnin D. et al., AMP-1c-120: An Antibody Specific for Misfolded Prion Protein Expressed on Ovarian Cancer Cells. Presented at the AACR 104th Annual Meeting in Washington DC on Apr. 9, 2013.

* cited by examiner

*Primary Examiner* — Kimberly A. Ballard
(74) *Attorney, Agent, or Firm* — Bereskin & Parr LLP; Carmela De Luca

(57) ABSTRACT

Human prion protein, PrP, selectively presents the epitope MDEYSNQNN (SEQ ID No. 14) when PrP misfolds. The misfolded form of human PrP is associated with various disease states. The present invention provides an antibody useful to detect and treat such diseases, including cancer such as ovarian cancer and lymphomas, and transmissible spongiform encephalopathies such as CJD. Also provided is an immunoconjugate in which the antibody is conjugated with urease as cytotoxin.

18 Claims, 12 Drawing Sheets

```
                        SEQUENCE LISTING

<160> NUMBER OF SEQ ID NOS: 14

<210> SEQ ID NO 1
<211> LENGTH: 5
<212> TYPE: PRT
<213> ORGANISM: oryctolagus cuniculus

<400> SEQUENCE: 1

Thr Tyr Ala Met Gly
1               5

<210> SEQ ID NO 2
<211> LENGTH: 16
<212> TYPE: PRT
<213> ORGANISM: oryctolagus cuniculus

<400> SEQUENCE: 2

Val Ile Thr Lys Ser Gly Asn Thr Tyr Tyr Ala Ser Trp Ala Lys Gly
1               5                   10                  15

<210> SEQ ID NO 3
<211> LENGTH: 10
<212> TYPE: PRT
<213> ORGANISM: oryctolagus cuniculus

<400> SEQUENCE: 3

Tyr Gly Ile Gly Val Ser Tyr Tyr Asp Ile
1               5                   10

<210> SEQ ID NO 4
<211> LENGTH: 13
<212> TYPE: PRT
<213> ORGANISM: oryctolagus cuniculus

<400> SEQUENCE: 4

Gln Ser Ser Gln Ser Leu Tyr Asn Lys Asn Trp Leu Ser
1               5                   10

<210> SEQ ID NO 5
<211> LENGTH: 7
<212> TYPE: PRT
<213> ORGANISM: oryctolagus cuniculus

<400> SEQUENCE: 5

Lys Ala Ser Thr Leu Glu Ser
1               5

<210> SEQ ID NO 6
<211> LENGTH: 13
```

<212> TYPE: PRT
<213> ORGANISM: oryctolagus cuniculus

<400> SEQUENCE: 6

Gln Gly Glu Phe Ser Cys Ser Ser Ala Asp Cys Thr Ala
1               5                   10

<210> SEQ ID NO 7
<211> LENGTH: 134
<212> TYPE: PRT
<213> ORGANISM: oryctolagus cuniculus

<400> SEQUENCE: 7

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
                20                  25                  30

Val Ser Ala Ala Val Gly Gly Thr Val Thr Ile Asn Cys Gln Ser Ser
            35                  40                  45

Gln Ser Leu Tyr Asn Lys Asn Trp Leu Ser Trp Tyr Gln Lys Lys Pro
        50                  55                  60

Gly Gln Pro Pro Lys Leu Leu Ile Tyr Lys Ala Ser Thr Leu Glu Ser
65                  70                  75                  80

Gly Val Ser Ser Arg Phe Lys Gly Ser Gly Ser Gly Thr Gln Phe Thr
                85                  90                  95

Leu Thr Ile Ser Gly Val Gln Cys Asp Asp Ala Ala Thr Tyr Tyr Cys
            100                 105                 110

Gln Gly Glu Phe Ser Cys Ser Ser Ala Asp Cys Thr Ala Phe Gly Gly
        115                 120                 125

Gly Thr Glu Val Val Val
    130

<210> SEQ ID NO 8
<211> LENGTH: 136
<212> TYPE: PRT
<213> ORGANISM: oryctolagus cuniculus

<400> SEQUENCE: 8

Met Glu Thr Gly Leu Arg Trp Leu Leu Leu Val Ala Val Leu Lys Gly
1               5                   10                  15

Val Gln Cys Gln Ser Val Glu Glu Ser Gly Gly His Leu Val Thr Pro
                20                  25                  30

Gly Thr Pro Leu Thr Leu Thr Cys Thr Val Ser Gly Ile Asp Leu Ser
            35                  40                  45

Thr Tyr Ala Met Gly Trp Val Arg Gln Ala Pro Gly Lys Gly Leu Glu
        50                  55                  60

Trp Ile Gly Val Ile Thr Lys Ser Gly Asn Thr Tyr Tyr Ala Ser Trp
65                  70                  75                  80

Ala Lys Gly Arg Phe Ala Ile Ser Lys Thr Ser Thr Val Asp Leu
                85                  90                  95

Lys Ile Thr Ser Pro Thr Thr Glu Asp Thr Ala Thr Tyr Phe Cys Gly
            100                 105                 110

Arg Tyr Gly Ile Gly Val Ser Tyr Tyr Asp Ile Trp Gly Pro Gly Thr
        115                 120                 125

Leu Val Thr Val Ser Ser Gly Gln
    130                 135

<210> SEQ ID NO 9
<211> LENGTH: 239
<212> TYPE: PRT
<213> ORGANISM: oryctolagus cuniculus

<400> SEQUENCE: 9

Met Asp Thr Arg Ala Pro Thr Gln Leu Gly Leu Leu Leu Leu Trp
1               5                   10                  15

Leu Pro Gly Ala Thr Phe Ala Gln Val Leu Thr Gln Thr Pro Ser Pro
            20                  25                  30

Val Ser Ala Ala Val Gly Gly Thr Val Thr Ile Asn Cys Gln Ser Ser
        35                  40                  45

Gln Ser Leu Tyr Asn Lys Asn Trp Leu Ser Trp Tyr Gln Lys Lys Pro
    50                  55                  60

Gly Gln Pro Pro Lys Leu Leu Ile Tyr Lys Ala Ser Thr Leu Glu Ser
65                  70                  75                  80

Gly Val Ser Ser Arg Phe Lys Gly Ser Gly Ser Gly Thr Gln Phe Thr
                85                  90                  95

Leu Thr Ile Ser Gly Val Gln Cys Asp Asp Ala Ala Thr Tyr Tyr Cys
            100                 105                 110

Gln Gly Glu Phe Ser Cys Ser Ser Ala Asp Cys Thr Ala Phe Gly Gly
        115                 120                 125

Gly Thr Glu Val Val Val Lys Gly Asp Pro Val Ala Pro Thr Val Leu
    130                 135                 140

Ile Phe Pro Pro Ala Ala Asp Gln Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235

<210> SEQ ID NO 10
<211> LENGTH: 457
<212> TYPE: PRT
<213> ORGANISM: oryctolagus cuniculus

<400> SEQUENCE: 10

Met Glu Thr Gly Leu Arg Trp Leu Leu Leu Val Ala Val Leu Lys Gly
1               5                   10                  15

Val Gln Cys Gln Ser Val Glu Glu Ser Gly Gly His Leu Val Thr Pro
            20                  25                  30

Gly Thr Pro Leu Thr Leu Thr Cys Thr Val Ser Gly Ile Asp Leu Ser
        35                  40                  45

Thr Tyr Ala Met Gly Trp Val Arg Gln Ala Pro Gly Lys Gly Leu Glu
    50                  55                  60

Trp Ile Gly Val Ile Thr Lys Ser Gly Asn Thr Tyr Tyr Ala Ser Trp
65                  70                  75                  80

Ala Lys Gly Arg Phe Ala Ile Ser Lys Thr Ser Thr Thr Val Asp Leu
                85                  90                  95

Lys Ile Thr Ser Pro Thr Thr Glu Asp Thr Ala Thr Tyr Phe Cys Gly

-continued

```
                   100                 105                 110
    Arg Tyr Gly Ile Gly Val Ser Tyr Tyr Asp Ile Trp Gly Pro Gly Thr
                       115                 120                 125

Leu Val Thr Val Ser Ser Gly Gln Pro Lys Ala Pro Ser Val Phe Pro
        130                 135                 140

Leu Ala Pro Cys Cys Gly Asp Thr Pro Ser Ser Thr Val Thr Leu Gly
    145                 150                 155                 160

Cys Leu Val Lys Gly Tyr Leu Pro Glu Pro Val Thr Val Thr Trp Asn
                    165                 170                 175

Ser Gly Thr Leu Thr Asn Gly Val Arg Thr Phe Pro Ser Val Arg Gln
                180                 185                 190

Ser Ser Gly Leu Tyr Ser Leu Ser Ser Val Val Ser Val Thr Ser Ser
            195                 200                 205

Ser Gln Pro Val Thr Cys Asn Val Ala His Pro Ala Thr Asn Thr Lys
        210                 215                 220

Val Asp Lys Thr Val Ala Pro Ser Thr Cys Ser Lys Pro Thr Cys Pro
    225                 230                 235                 240

Pro Pro Glu Leu Leu Gly Gly Pro Ser Val Phe Ile Phe Pro Pro Lys
                    245                 250                 255

Pro Lys Asp Thr Leu Met Ile Ser Arg Thr Pro Glu Val Thr Cys Val
                260                 265                 270

Val Val Asp Val Ser Gln Asp Asp Pro Glu Val Gln Phe Thr Trp Tyr
            275                 280                 285

Ile Asn Asn Glu Gln Val Arg Thr Ala Arg Pro Pro Leu Arg Glu Gln
        290                 295                 300

Gln Phe Asn Ser Thr Ile Arg Val Val Ser Thr Leu Pro Ile Ala His
    305                 310                 315                 320

Gln Asp Trp Leu Arg Gly Lys Glu Phe Lys Cys Lys Val His Asn Lys
                    325                 330                 335

Ala Leu Pro Ala Pro Ile Glu Lys Thr Ile Ser Lys Ala Arg Gly Gln
                340                 345                 350

Pro Leu Glu Pro Lys Val Tyr Thr Met Gly Pro Pro Arg Glu Glu Leu
            355                 360                 365

Ser Ser Arg Ser Val Ser Leu Thr Cys Met Ile Asn Gly Phe Tyr Pro
        370                 375                 380

Ser Asp Ile Ser Val Glu Trp Glu Lys Asn Gly Lys Ala Glu Asp Asn
    385                 390                 395                 400

Tyr Lys Thr Thr Pro Ala Val Leu Asp Ser Asp Gly Ser Tyr Phe Leu
                    405                 410                 415

Tyr Ser Lys Leu Ser Val Pro Thr Ser Glu Trp Gln Arg Gly Asp Val
                420                 425                 430

Phe Thr Cys Ser Val Met His Glu Ala Leu His Asn His Tyr Thr Gln
            435                 440                 445

Lys Ser Ile Ser Arg Ser Pro Gly Lys
        450                 455
```

<210> SEQ ID NO 11
<211> LENGTH: 1374
<212> TYPE: DNA
<213> ORGANISM: synthetic construct

<400> SEQUENCE: 11

| | | | | | |
|---|---|---|---|---|---|
| atggagactg | ggctgcgctg | gcttctcctg | gtcgctgtgc | tcaaaggtgt | ccagtgtcag | 60 |
| tcggtggagg | agtccggggg | gtcacctggtc | acgcctggga | caccccctgac | actcacctgc | 120 |

```
acagtctctg gaatcgacct cagtacctat gcaatgggct gggtccgcca ggctccaggg      180
aaggggctgg agtggatcgg agtcattact aaaagtggta acacatacta cgcgagctgg      240
gcgaaaggcc gattcgccat ctccaaaacc tcgaccacgg tggatctaaa gatcaccagt      300
ccgacaaccg aggacacggc cacctatttc tgtggcagat atggtattgg tgtttcttac      360
tatgacatct ggggcccagg cactctggtc accgtctcct cagggcaacc taaggctcca      420
tcagtcttcc cactggcccc ctgctgcggg gacacaccca gctccacggt gaccctgggc      480
tgcctggtca agggtacctc ccggagcca gtgaccgtga cctggaactc gggcaccctc      540
accaatgggg tacgcacctt cccgtccgtc cggcagtcct caggcctcta ctcgctgagc      600
agcgtggtga gcgtgacctc aagcagccag cccgtcacct gcaacgtggc cacccagcc      660 accaacacca aagtggacaa gaccgttgcg ccctcgacat gcagcaagcc cacgtgccca      720
ccccctgaac tcctgggggg accgtctgtc ttcatcttcc ccccaaaacc caaggacacc      780
ctcatgatct cacgcacccc cgaggtcaca tgcgtggtgg tggacgtgag ccaggatgac      840
cccgaggtgc agttcacatg gtacataaac aacgagcagg tgcgcaccgc ccggccgccg      900
ctacgggagc agcagttcaa cagcacgatc cgcgtggtca gcaccctccc catcgcgcac      960
caggactggc tgaggggcaa ggagttcaag tgcaaagtcc acaacaaggc actcccggcc     1020
cccatcgaga aaaccatctc caaagccaga gggcagcccc tggagccgaa ggtctacacc     1080
atgggccctc ccgggagga gctgagcagc aggtcggtca gcctgacctg catgatcaac     1140
ggcttctacc cttccgacat ctcggtggag tgggagaaga cgggaaggc agaggacaac     1200 tacaagacca cgccggccgt gctggacagc gacggctcct acttcctcta cagcaagctc     1260
tcagtgccca cgagtgagtg gcagcggggc gacgtcttca cctgctccgt gatgcacgag     1320
gccttgcaca accactacac gcagaagtcc atctcccgct ctccgggtaa atga           1374
```

<210> SEQ ID NO 12
<211> LENGTH: 720
<212> TYPE: DNA
<213> ORGANISM: synthetic construct

<400> SEQUENCE: 12

```
atggacacga gggcccccac tcagctgctg ggctcctgc tgctctggct cccaggtgcc       60
acatttgccc aagtgctgac ccagactcca tcccctgtgt ctgcagctgt gggaggcaca      120
gtcaccatca attgccagtc cagtcagagt ctttataata gaactggtt atcctggtat      180 cagaagaaac cagggcagcc tcctaagctc ctgatctaca aggcatccac tctggaatct      240
ggggtctcat cgcggttcaa gggcagtgga tctgggacac agttcactct caccatcagc      300
ggcgtgcagt gtgacgatgc tgccacttac tactgtcaag cgaatttag ttgtagtagt      360 gctgattgta cggctttcgg cggagggacc gaggtggtgg tcaaaggtga tccagttgca      420
cctactgtcc tcatcttccc accagctgct gatcaggtgg caactggaac agtcaccatc      480
gtgtgtgtgg cgaataaata ctttcccgat gtcaccgtca cctgggaggt ggatggcacc      540
acccaaacaa ctggcatcga gaacagtaaa acaccgcaga attctgcaga ttgtacctac      600
aacctcagca gcactctgac actgaccagc acacagtaca cagccacaa agagtacacc      660 tgcaaggtga cccagggcac gacctcagtc gtccagagct tcaataggg tgactgttag      720
```

<210> SEQ ID NO 13
<211> LENGTH: 840
<212> TYPE: PRT

<213> ORGANISM: canavalia ensiformis

<400> SEQUENCE: 13

```
Met Lys Leu Ser Pro Arg Glu Val Glu Lys Leu Gly Leu His Asn Ala
1               5                   10                  15

Gly Tyr Leu Ala Gln Lys Arg Leu Ala Arg Gly Val Arg Leu Asn Tyr
                20                  25                  30

Thr Glu Ala Val Ala Leu Ile Ala Ser Gln Ile Met Glu Tyr Ala Arg
            35                  40                  45

Asp Gly Glu Lys Thr Val Ala Gln Leu Met Cys Leu Gly Gln His Leu
        50                  55                  60

Leu Gly Arg Arg Gln Val Leu Pro Ala Val Pro His Leu Leu Asn Ala
65                  70                  75                  80

Val Gln Val Glu Ala Thr Phe Pro Asp Gly Thr Lys Leu Val Thr Val
                85                  90                  95

His Asp Pro Ile Ser Arg Glu Asn Gly Glu Leu Gln Glu Ala Leu Phe
            100                 105                 110

Gly Ser Leu Leu Pro Val Pro Ser Leu Asp Lys Phe Ala Glu Thr Lys
        115                 120                 125

Glu Asp Asn Arg Ile Pro Gly Glu Ile Leu Cys Glu Asp Glu Cys Leu
    130                 135                 140

Thr Leu Asn Ile Gly Arg Lys Ala Val Ile Leu Lys Val Thr Ser Lys
145                 150                 155                 160

Gly Asp Arg Pro Ile Gln Val Gly Ser His Tyr His Phe Ile Glu Val
                165                 170                 175

Asn Pro Tyr Leu Thr Phe Asp Arg Arg Lys Ala Tyr Gly Met Arg Leu
            180                 185                 190

Asn Ile Ala Ala Gly Thr Ala Val Arg Phe Glu Pro Gly Asp Cys Lys
        195                 200                 205

Ser Val Thr Leu Val Ser Ile Glu Gly Asn Lys Val Ile Arg Gly Gly
    210                 215                 220

Asn Ala Ile Ala Asp Gly Pro Val Asn Glu Thr Asn Leu Glu Ala Ala
225                 230                 235                 240

Met His Ala Val Arg Ser Lys Gly Phe Gly His Glu Glu Glu Lys Asp
                245                 250                 255

Ala Ser Glu Gly Phe Thr Lys Asp Pro Asn Cys Pro Phe Asn Thr
            260                 265                 270

Phe Ile His Arg Lys Glu Tyr Ala Asn Lys Tyr Gly Pro Thr Thr Gly
        275                 280                 285

Asp Lys Ile Arg Leu Gly Asp Thr Asn Leu Leu Ala Glu Ile Glu Lys
    290                 295                 300

Asp Tyr Ala Leu Tyr Gly Asp Glu Cys Val Phe Gly Gly Gly Lys Val
305                 310                 315                 320

Ile Arg Asp Gly Met Gly Gln Ser Cys Gly His Pro Pro Ala Ile Ser
                325                 330                 335

Leu Asp Thr Val Ile Thr Asn Ala Val Ile Asp Tyr Thr Gly Ile
            340                 345                 350

Ile Lys Ala Asp Ile Gly Ile Lys Asp Gly Leu Ile Ala Ser Ile Gly
        355                 360                 365

Lys Ala Gly Asn Pro Asp Ile Met Asn Gly Val Phe Ser Asn Met Ile
    370                 375                 380

Ile Gly Ala Asn Thr Glu Val Ile Ala Gly Glu Gly Leu Ile Val Thr
385                 390                 395                 400
```

```
Ala Gly Ala Ile Asp Cys His Val His Tyr Ile Cys Pro Gln Leu Val
                405                 410                 415
Tyr Glu Ala Ile Ser Ser Gly Ile Thr Thr Leu Val Gly Gly Thr
            420                 425                 430
Gly Pro Ala Ala Gly Thr Arg Ala Thr Thr Cys Thr Pro Ser Pro Thr
            435                 440                 445
Gln Met Arg Leu Met Leu Gln Ser Thr Asp Asp Leu Pro Leu Asn Phe
    450                 455                 460
Gly Phe Thr Gly Lys Gly Ser Ser Ser Lys Pro Asp Glu Leu His Glu
465                 470                 475                 480
Ile Ile Lys Ala Gly Ala Met Gly Leu Lys Leu His Glu Asp Trp Gly
                485                 490                 495
Ser Thr Pro Ala Ala Ile Asp Asn Cys Leu Thr Ile Ala Glu His His
            500                 505                 510
Asp Ile Gln Ile Asn Ile His Thr Asp Thr Leu Asn Glu Ala Gly Phe
        515                 520                 525
Val Glu His Ser Ile Ala Ala Phe Lys Gly Arg Thr Ile His Thr Tyr
    530                 535                 540
His Ser Glu Gly Ala Gly Gly Gly His Ala Pro Asp Ile Ile Lys Val
545                 550                 555                 560
Cys Gly Ile Lys Asn Val Leu Pro Ser Ser Thr Asn Pro Thr Arg Pro
                565                 570                 575
Leu Thr Ser Asn Thr Ile Asp Glu His Leu Asp Met Leu Met Val Cys
            580                 585                 590
His His Leu Asp Arg Glu Ile Pro Glu Asp Leu Ala Phe Ala His Ser
        595                 600                 605
Arg Ile Arg Lys Lys Thr Ile Ala Ala Glu Asp Val Leu Asn Asp Ile
    610                 615                 620
Gly Ala Ile Ser Ile Ile Ser Ser Asp Ser Gln Ala Met Gly Arg Val
625                 630                 635                 640
Gly Glu Val Ile Ser Arg Thr Trp Gln Thr Ala Asp Lys Met Lys Ala
                645                 650                 655
Gln Thr Gly Pro Leu Lys Cys Asp Ser Ser Asp Asn Asp Asn Phe Arg
            660                 665                 670
Ile Arg Arg Tyr Ile Ala Lys Tyr Thr Ile Asn Pro Ala Ile Ala Asn
        675                 680                 685
Gly Phe Ser Gln Tyr Val Gly Ser Val Glu Val Gly Lys Leu Ala Asp
    690                 695                 700
Leu Val Met Trp Lys Pro Ser Phe Phe Gly Thr Lys Pro Glu Met Val
705                 710                 715                 720
Ile Lys Gly Gly Met Val Ala Trp Ala Asp Ile Gly Asp Pro Asn Ala
                725                 730                 735
Ser Ile Pro Thr Pro Glu Pro Val Lys Met Arg Pro Met Tyr Gly Thr
            740                 745                 750
Leu Gly Lys Ala Gly Gly Ala Leu Ser Ile Ala Phe Val Ser Lys Ala
        755                 760                 765
Ala Leu Asp Gln Arg Val Asn Val Leu Tyr Gly Leu Asn Lys Arg Val
    770                 775                 780
Glu Ala Val Ser Asn Val Arg Lys Leu Thr Lys Leu Asp Met Lys Leu
785                 790                 795                 800
Asn Asp Ala Leu Pro Glu Ile Thr Val Asp Pro Glu Ser Tyr Thr Val
                805                 810                 815
Lys Ala Asp Gly Lys Leu Leu Cys Val Ser Glu Ala Thr Thr Val Pro
```

-continued

```
        820                 825                 830

Leu Ser Arg Asn Tyr Phe Leu Phe
        835                 840

<210> SEQ ID NO 14
<211> LENGTH: 9
<212> TYPE: PRT
<213> ORGANISM: Homo Sapien
<400> SEQUENCE: 14

Met Asp Glu Tyr Ser Asn Gln Asn Asn
1               5
```

ANTIBODIES AND CONJUGATES THAT TARGET MISFOLDED PRION PROTEIN

RELATED APPLICATIONS

This PCT application claims the benefit of priority from U.S. Provisional Application filed under Ser. No. 61/658,569 on Jun. 12, 2012 and from U.S. Provisional Application filed under Ser. No. 61/809,604 on Apr. 8, 2013, each of which are incorporated herein by reference in their entirety.

FIELD OF THE INVENTION

This invention relates to antibodies having therapeutic and diagnostic utility. More particularly, the present invention relates to antibodies that bind selectively to an epitope presented uniquely by a misfolded form of the human PrP protein. The antibodies, binding fragments thereof and immunoconjugates based thereon are useful therapeutically and diagnostically in the treatment and detection of cancer, as well as diseases associated with PrP misfolding and aggregation that include the transmissible spongiform encephalopathies, such as Creutzfeldt-Jakob disease (CJD).

BACKGROUND TO THE INVENTION

About one-third of the population of the developed world is destined to die from cancer. Current treatment for cancers—including chemotherapy and radiotherapy—are based on killing cancer cells preferentially to normal cells, the so-called "therapeutic window" which accepts significant adverse effects for even marginal slowing of tumor growth. Specific treatments that spare normal cells are urgently needed.

Cancer cells are different from normal cells in many ways, including a propensity for protein misfolding, intracellularly and at the cell surface. Such misfolded proteins may be the consequence of germ cell or somatic mutation, chromosomal translocation or aneuploidy, mutagenic effects of chemotherapy or radiation therapy, titration of chaperones, molecular crowding in the endoplasmic reticulum and other secretory compartments including the cell surface, aberrant glycosylation and trafficking, impaired clearance and/or degradation, environmental stressors or allosteric influences relevant to the tumor bed (such as lowered pH or increased ligand concentration), and post-translational modifications including oxidation and nitration of select residues. All or some of these factors relevant to cancer contribute to greater dynamic fluctuation and net solvent exposure of specific regions of proteins which are normally rarely accessible in non-cancerous cells. Antibody recognition of these abnormally exposed protein motifs, designated Disease Specific Epitopes (DSE), will serve as a diagnostic cancer marker or cancer treatment target, and provide insight into abnormal cell growth in cancer and other diseases.

A disease specific epitope for the prion protein (PrP) has recently been described as a diagnostic and treatment target for the transmissible spongiform encephalopathies (Paramithiotis et al, Nature Medicine 2003, 9(7):893). This prion DSE, defined by the core trimer YYR, is an epitope exposed on the molecular surface of disease-misfolded $PrP^{Sc}$, but is buried in the antibody-inaccessible interior of the normal prion protein $PrP^C$. $PrP^C$ is abundantly expressed by normal circulating lymphoid and myeloid cells (Cashman et al, Cell 1990, 61(1):185), and plays a role in hematopoietic differentiation from CD34+ bone marrow stem cells (Dodelet and Cashman, Blood 1998, 91(5):1556). However, YYR surface immunoreactivity had never been detected on any normal cell, including splenocytes of mixed lineage, and dissociated brain cells.

US 2009/0175884 establishes that certain cancer cells are reactive with antibodies raised against the YYR epitope unique to the misfolded form of PrP, and proposes the use of YYR antibodies to inhibit the growth and/or proliferation of those cancer cells. The production of YYR antibodies and their use to control progression of PrP aggregation, as a way of treating transmissible spongiform encephalopathies such as Creutzfeldt-Jakob disease (CJD) was first described in U.S. Pat. No. 7,041,807. WO 2010/099612 identifies and proposes the targeting of another cryptic epitope that is exposed when PrP misfolds, i.e., the trimer YML. Also, WO 2010/04020 describes an algorithm useful to predict misfolding "hot spots" in a variety of target proteins, including PrP. Those inventors suggest targeting the predicted disease specific epitopes using antibodies, for instance, as a means for treating diseases in which the misfolding of that target protein is implicated.

It is an object of the present invention to provide antibodies, and fragments and conjugates thereof that bind selectively to a misfolded form of PrP.

It is a further object of the present invention to provide such antibodies, fragments and conjugates as compositions, particularly for therapeutic and diagnostic use.

It is a further object of the present invention to provide a method useful, in a subject in need thereof, to control the growth and/or proliferation of disease cells that present misfolded PrP on their surface.

It is a further object of the present invention to provide a method useful, in a subject in need thereof, to control the progression of PrP aggregation, as a means of treating diseases in which aggregation of PrP is implicated, such as the transmissible spongiform encephalopathies.

SUMMARY OF THE INVENTION

The present invention provides an antibody that binds selectively to a misfolded form of PrP. More particularly, there is now provided an antibody that binds selectively to an epitope that is presented by PrP only in its misfolded state. The antibody displays little to no affinity for binding to PrP in its wild type, natively folded conformation. The epitope is defined by the amino acid sequence MDEYSNQNN (SEQ ID NO. 14), which resides in a region of PrP known as the rigid loop. It has been found that antibodies raised against this epitope display a binding preference for misfolded PrP. These antibodies, as well as their binding fragments and immunoconjugates based thereon, find utility in a variety of diagnostic and therapeutic applications.

Thus, in a first aspect, the present invention provides an antibody characterized by binding selectivity for an epitope comprising the sequence MDEYSNQNN (SEQ ID No. 14), the antibody comprising a heavy chain and a light chain, each chain having a constant region and a variable region, each variable region comprising framework regions and complementarity determining regions (CDRs), wherein the CDRs have an amino acid sequence set forth below:

For the heavy chain:

| CDR1 | TYAMG           | (SEQ ID No. 1) |
|------|-----------------|----------------|
| CDR2 | VITKSGNTYYASWAKG | (SEQ ID No. 2) |
| CDR3 | YGIGVSYYDI      | (SEQ ID No. 3) |

For the light chain:

```
CDR1    QSSQSLYNKNWLS    (SEQ ID No. 4)
CDR2    KASTLES          (SEQ ID No. 5)
CDR3    QGEFSCSSADCTA    (SEQ ID No. 6)
```

In embodiments, the present invention provides a PrP antibody comprising a heavy chain and a light chain, each chain having a constant region and a variable region, wherein the heavy chain variable region comprises the sequence of SEQ ID No. 8 and the light chain variable region comprises the sequence of SEQ ID No. 7. The present antibody thus comprises CDR1, CDR2 and CDR3 residing in SEQ ID No. 7, and CDR1, CDR2 and CDR3 residing in SEQ ID No. 8. The precise sequence of those CDRs is determined using practices standard in the antibody art. The location of the CDRs within the antibody is determined by numbering amino acid residues with reference to the Kabat numbering system.

This antibody, herein designated ab120, displays both an affinity for binding to ovarian cancer cells that present a misfolded form of PrP, and a clear preference for binding to those ovarian cancer cells, relative to normal ovarian epithelial cells. The antibody is thus very well suited for use in ovarian cancer detection and treatment.

In related aspects, the present invention provides fragments of the present antibody that retain binding affinity and selectivity for misfolded PrP, as well as immunoconjugates that incorporate the present antibody or antibody fragment. In embodiments, the antibody fragment is a monovalent or a bivalent antibody fragment. In other embodiments, the immunoconjugate comprises the present antibody or antibody fragment conjugated with an agent useful to treat or detect misfolded PrP. The agent can be a toxin or any detectable label. The immunoconjugate can be useful to detect misfolded PrP as a protein per se in a sample, or as a disease cell surface protein on intact cells and tissues.

In a particular aspect, the present invention further provides an immunoconjugate, comprising urease and, conjugated therewith, an antigen binding site from an antibody of the present invention.

In a further aspect, the present antibody, binding fragment or immunoconjugate are formulated for use, and thus are provided as compositions that further comprise a pharmaceutically acceptable carrier for subsequent medical use, or a physiologically tolerable vehicle for subsequent diagnostic use.

In another aspect, the present invention provides a method for controlling the growth or proliferation of a disease cell that presents a misfolded form of PrP (i.e., has a misfolded PrP+ phenotype) in which the rigid loop is antibody-accessible, comprising treating the disease cell with an amount of the present antibody, fragment or immunoconjugate effective to control the growth and/or proliferation of that disease cell. In a related aspect, the present method is used for the treatment of cancer cells that are positive for misfolded PrP. In embodiments, the antibody, fragment or conjugate is used for the treatment of ovarian cancer particularly.

In another aspect, the present invention provides a method for controlling the propagation of PrP misfolding or progression of endogenous PrP aggregation in the transmissible spongiform encephalopathies, comprising the step of exposing misfolded PrP to an amount of the present antibody effective to inhibit PrP aggregation. In a related aspect, the present invention provides a method for inhibiting progression of endogenous PrP aggregation, by administering to a subject the present antibody in an amount sufficient to effect clearance of misfolded PrP, or aggregates thereof.

In other aspects, the present invention provides an assay for detecting misfolded PrP in a sample, the assay comprising the steps of: (a) contacting the sample with an antibody, fragment or immunoconjugate thereof that binds to an epitope comprising the amino acid sequence MDEYSNQNN (SEQ ID No. 14) of human PrP under conditions that allow for complex formation between said antibody and misfolded PrP, and (b) detecting complex formation, the presence of which is indicative of the presence of misfolded PrP in the sample.

In still other aspects, the present invention provides a screening method for identifying a subject having a condition in which PrP misfolding is implicated, such as prion disease and cancer, the method comprising the step of detecting misfolded PrP in a biological sample obtained from that subject, the method comprising the steps of: (a) contacting the biological sample with an antibody, fragment or immunoconjugate thereof that binds to an epitope comprising the amino acid sequence MDEYSNQNN (SEQ ID No. 14) of human PrP under conditions that allow for complex formation between said antibody and misfolded PrP, and (b) detecting complex formation, the presence of which is indicative of the presence of misfolded PrP in the sample.

In related aspects, the present invention provides a kit useful for performing the assay and screening methods of the invention, the kit comprising an antibody according to the invention, or a binding fragment or immunoconjugate thereof, and instructions for the use thereof in accordance with the assay or screening methods herein described.

These and other aspects of the present invention are now described in greater detail with reference to the accompanying drawings, in which:

REFERENCE TO THE FIGURES

FIG. 1 shows evaluation of rabbit antisera. A. Preimmune (open boxes) and bleed 2 (filled boxes) rabbit antisera were tested for binding to BSA-DSE3 peptide. B. Bleed 2 antiserum was evaluated for binding to BSA (triangles) and denatured PrP (circles).

FIG. 2 shows anti-peptide binding of seven anti-DSE3 monoclonal antibodies. Each antibody was evaluated for binding to a BSA-irrelevant peptide (triangles) and BSA-DSE3 peptide (circles). A positive control anti-BSA antibody bound to both BSA-peptides.

FIG. 3 shows anti-PrP binding of seven anti-DSE3 monoclonal antibodies. Each antibody was evaluated for binding to denatured recombinant PrP (circles) and His-tagged captured PrP (triangles). A control anti-PrP antibody bound to both denatured PrP and His-tagged captured PrP.

FIG. 4 shows anti-PrP antibody binding to tumor and normal cells. The DSE3 ab120 antibody or a control anti-PrP antibody was incubated at 10 ug/mL with various cells. Antibody binding was detected using an anti-rabbit IgG-AF488 or anti-mouse IgG-AF488 secondary antibody, followed by fluorescence evaluation by flow cytometry (BD FACS Canto II).

FIG. 5 shows titration of antibody binding to tumor and normal cells. The DSE3 ab120 antibody or a control anti-PrP antibody (6H4) was incubated at varying concentrations with three tumor and two normal cells. Antibody detection was as described for FIG. 4.

FIG. 6 reveals the conformational state of PrP resident on the surface of various tumour cell lines as determined by proteinase K titration. As shown, proteinase K sensitivity is high for the N-terminal region (upward triangles), low for the C-terminal region (downward triangles), and intermediate for the rigid loop region (squares) within the forms of PrP tested.

Figure 9:
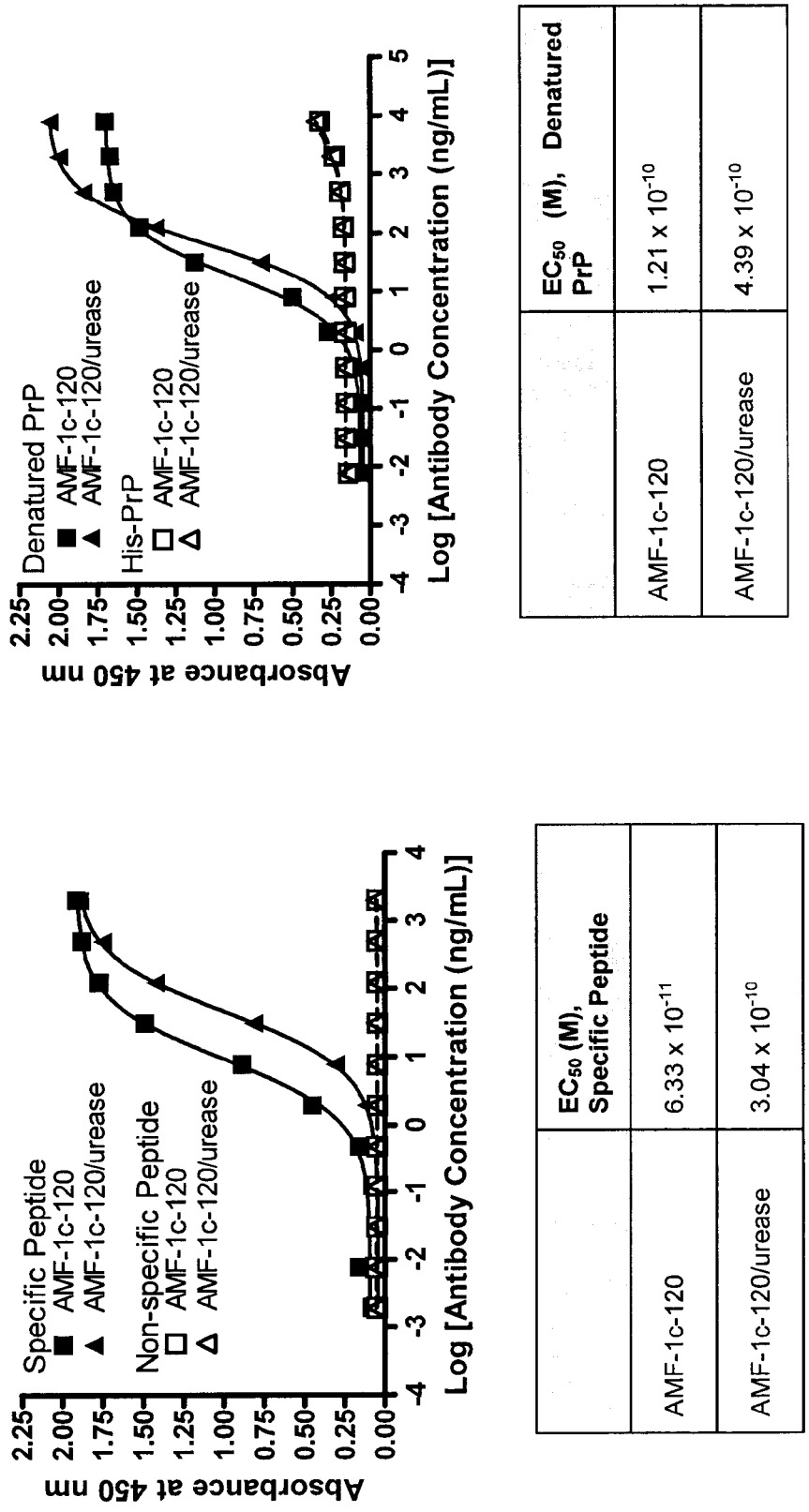
Figure 10:
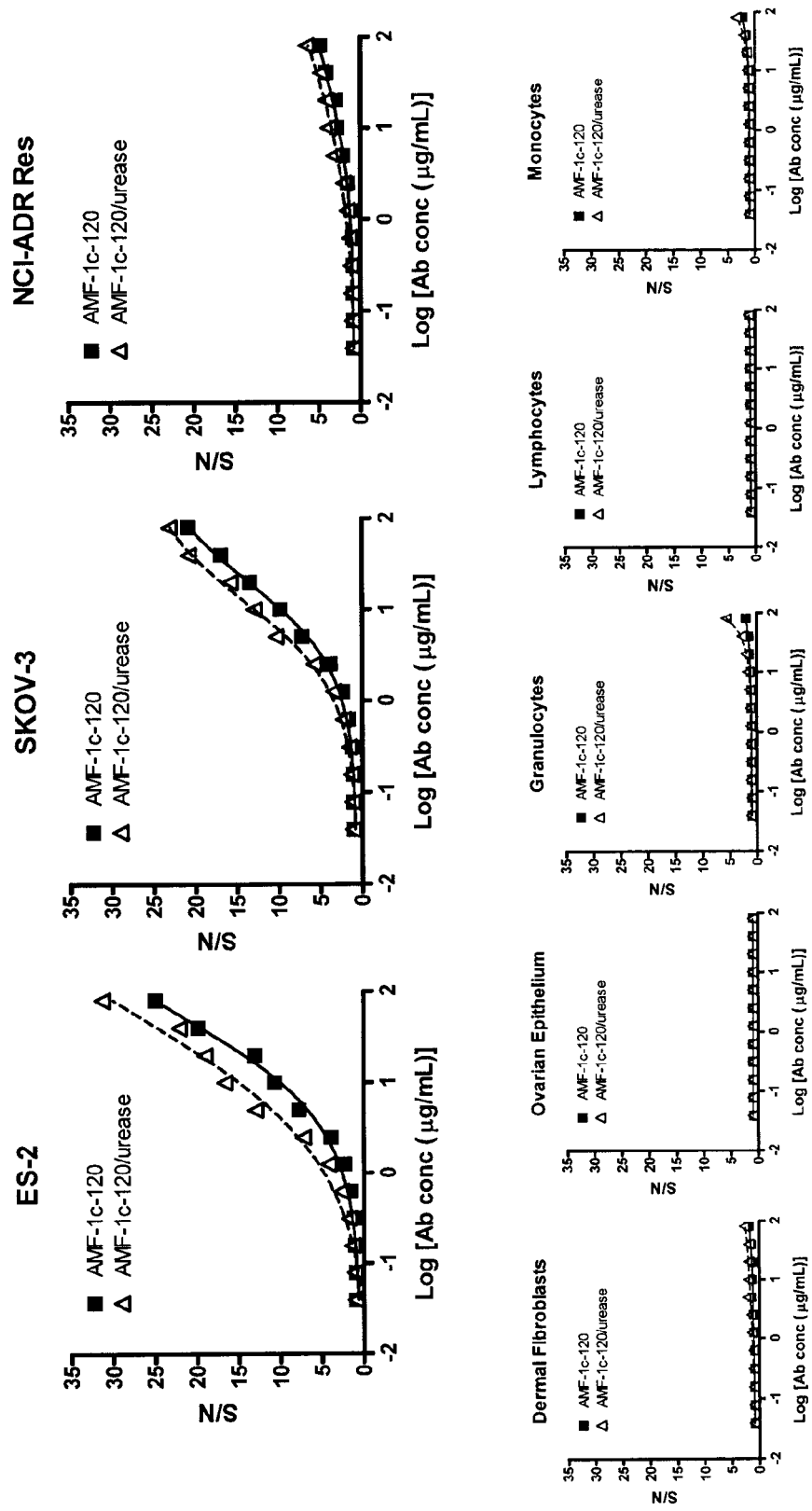

FIG. 9 reveals the binding characteristics of AMF-1c-120 conjugated to urease. A. AMF-1c-120 (squares) and AMF-1c-120/urease conjugate (triangles) binding to specific peptide (filled) and non-specific peptide (open). B. AMF-1c-120 (squares) and AMF-1c-120/urease (triangles) binding to denatured PrP (filled) and captured His-PrP (open);

FIG. 10 shows binding of AMF-1c-120 and AMF-1c-120/urease conjugate to tumor and normal cells. AMF-1c-120 or AMF-1c-120/urease conjugate was incubated at varying concentrations with three tumor and five normal cells. Antibody binding was detected using an anti-rabbit IgG-AF488 secondary antibody, followed by fluorescence evaluation by flow cytometry.

Figure 11:
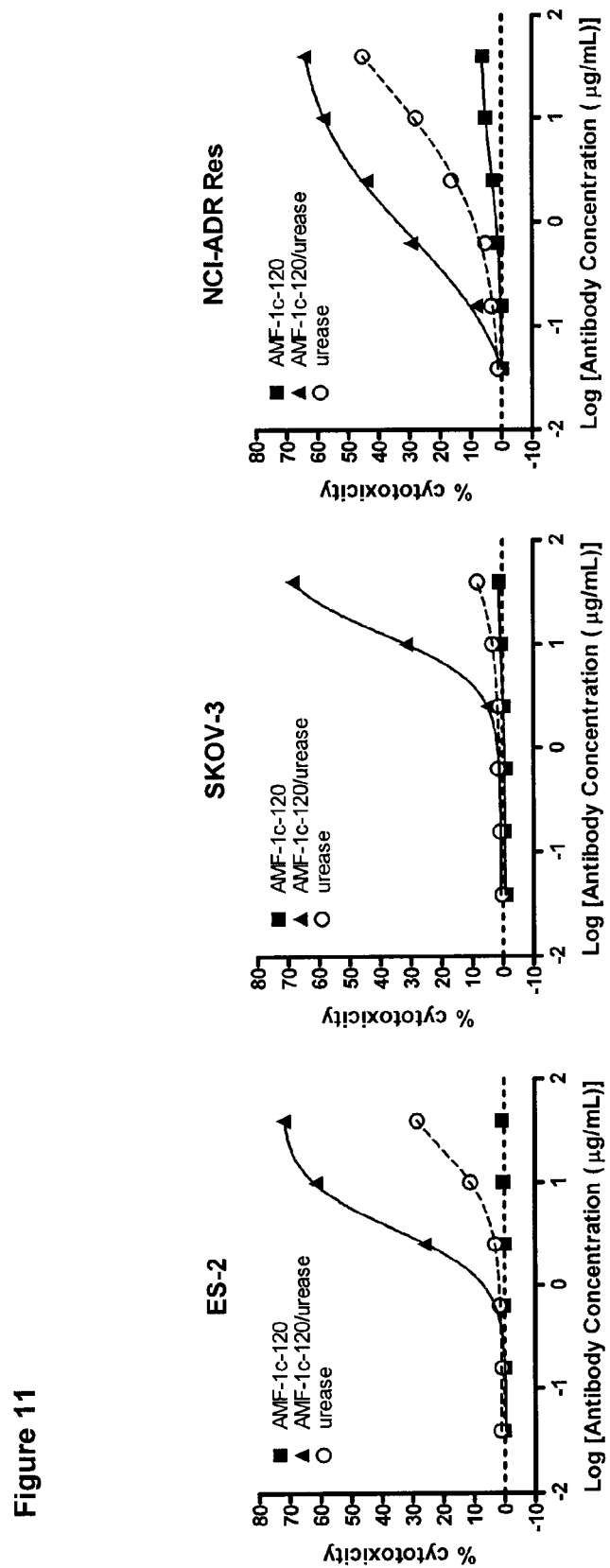

FIG. 11 reveals the cytotoxicity of AMF-1c-120/urease in vitro. AMF-1c-120, AMF-1c-120/urease conjugate or urease were incubated with tumor cells for two hours. Cells were washed twice and then incubated with 20 mM urea for 30 minutes. Cell viability was evaluated by addition of WST-1 followed by measuring absorbance after 16-20 hours.

Figure 12:
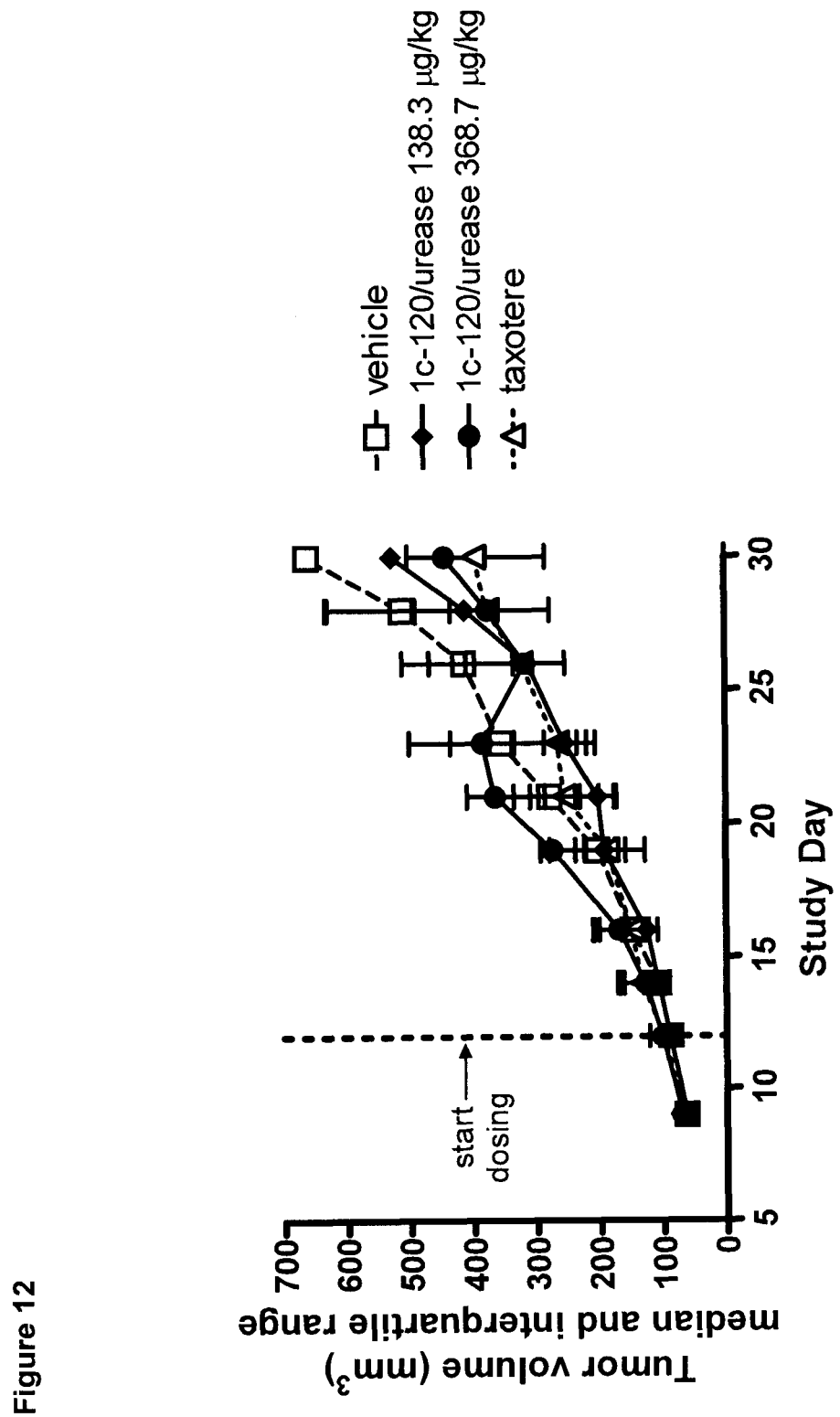

FIG. 12 shows the effect of 1c-120/urease therapy on ES-2 tumor growth in immunocompromised Rag2M mice. Mice were treated iv three times weekly with vehicle (squares), 1c-120/urease at 183.3 μg/kg (diamonds), 1c-120/urease at 368.7 μg/kg (circles) or taxotere (triangles). Tumor growth was monitored by measuring tumor dimensions with calipers. Tumor volumes were calculated according to the equation $L \times W^2/2$.

DETAILED DESCRIPTION OF THE INVENTION AND PREFERRED EMBODIMENTS

As used herein, the term "PrP" refers to a mature human protein that comprises the expressed and processed product of the PRP gene, wherein the mature protein is designated as residues 1-230 of UniProtKB/Swiss-Prot P04156. For present purposes, the term "PrP" further includes naturally occurring variants of this protein that, in a misfolded state, retain binding affinity for the present antibodies.

An "isolated antibody", as used herein, refers to an antibody that is substantially free of other antibodies having different antigenic specificities (e.g., an isolated antibody that specifically binds misfolded PrP is substantially free of antibodies that specifically bind antigens other than PrP proteins). An isolated antibody that specifically binds a misfolded human PrP protein may, however, have cross-reactivity to other antigens, such as misfolded PrP proteins from other species, but shows little or essentially no affinity for binding wild type human PrP. Moreover, an isolated antibody can be substantially free of other cellular material and/or chemicals. An isolated antibody also can be substantially free of other proteins of human origin.

The present invention relates to PrP antibodies that display an affinity and preference for binding to a form of PrP that presents an epitope comprising all or an antibody-binding part (comprising at least 5 contiguous residues) of the sequence MDEYSNQNN (SEQ ID No. 14) (sometimes referenced as DSE3). This region of the PrP protein is referred to as the "rigid loop", and represents residues 166-174 of the human prion protein. In its normal conformation, this epitope lies cryptically within the prion protein, but becomes accessible to the antibody when PrP misfolds, as a result for instance of local environmental shifts in conditions such as temperature or pH, or as a result of aberrant protein trafficking within the host cell or as a result of phenomena not yet understood. This misfolded form of PrP is found, for instance, on the surface of some PrP+ cancer cells. Its presence on disease cells provides a therapeutic and diagnostic target for the present antibody, and means for achieving this are provided by the present invention.

Thus, there is provided an antibody that comprises, as key features, an affinity for binding to the rigid loop of PrP, an affinity for binding to ovarian cancer cells that are misfolded PrP+, a preference for binding to ovarian cancer cells that are misfolded PrP+ relative to normal ovarian epithelial cells, and complementarity determining regions having the sequences first recited above.

In embodiments, the antibody is an intact antibody comprising features common to all natural antibodies, e.g., a heavy chain and a light chain, each chain having a constant region and a variable region, each variable region comprising framework regions (FRs) and complementarity determining regions (CDRs). In the alternative, the antibody is provided as a fragment that is either monovalent or is bivalent, i.e., an antibody fragment comprising both "arms" of an intact antibody, joined through a linker that can be represented by the hinge region of the antibody or any equivalent. Such bivalent fragments include F(ab)$_2$ fragments and any other bivalent fragment that retains preference for binding to misfolded PrP. In particular embodiments, the bivalent fragment is a F(ab')$_2$ fragment, generated for instance by papain-based digestion of the parent antibody using standard procedures for digestion and subsequent fragment isolation. In the alternative, the fragment can be a so-called single chain Fv (scFv), consisting of the variable light and variable heavy antibody domains joined by an amino acid linker, or a bivalent form of a so-called diabody prepared using a 5 amino acid linker such as SGGGG between the light and heavy chain variable domains and a C-terminal cysteine modification to GGC to give a final diabody product as VL-SGGG-VH-GGC. Still other bivalent fragments can be prepared by coupling the light and heavy chain variable domains through thioether linkages such as bis-maleimidomethyl ether (BMME), N,N'-p-phenylene dimaleimide (PDM and N,N'-bismaleimidohexane BMH), to stabilize the F(ab')2 fragments.

In the intact antibody or bivalent fragment, the CDRs comprise or consist of the following amino acid sequences:

For the heavy chain:

| CDR1 | TYAMG | (SEQ ID No. 1) |
| CDR2 | VITKSGNTYYASWAKG | (SEQ ID No. 2) |
| CDR3 | YGIGVSYYDI | (SEQ ID No. 3) |

For the light chain:

| CDR1 | QSSQSLYNKNWLS | (SEQ ID No. 4) |
| CDR2 | KASTLES | (SEQ ID No. 5) |
| CDR3 | QGEFSCSSADCTA | (SEQ ID No. 6) |

Some variation is tolerable within these sequences, such as one or two conservative amino acid substitutions per CDR, and as many as 1, 2 or 3 CDRs having such substitutions, but usually no more than about 5 substitutions within the CDRs collectively. It will be appreciated that the conservative amino acid families include (i) G, A, V, L and I; (ii) D and E; (iii) A, S and T; (iv) H, K and R; (v) N and Q; and (vi) F, Y and W. Thus, "conservative sequence modifications" can be made, and include amino acid modifications that do not significantly affect or alter the binding characteristics of the antibody containing the amino acid sequence. Such conservative modifications include amino acid substitutions, additions and deletions. Modifications can be introduced into an antibody of the invention at the genetic level by standard techniques known in the art, such as site-directed mutagenesis and PCR-mediated mutagenesis. In addition to the recited three CDRs present in each of the light and heavy chain variable regions, the heavy and light chains of the intact antibody comprise four intervening framework regions that present the CDRs in a conformation suitable for binding to the rigid loop of PrP, and constant regions that confer antibody effector function. The CDRs can be integrated into any suitable acceptor antibody, by grafting the present CDRs into the acceptor antibody, in accordance with practices and techniques well established for the production of chimeric, humanized and human antibodies.

It is well known in the art that the CDR3 domain alone can determine the binding specificity of an antibody for a cognate antigen and that multiple antibodies can predictably be generated having the same binding specificity based on a common CDR3 sequence. See, e.g., Klimka et al., *British J. of Cancer* 83(2):252-260 (2000); Beiboer et al., *J. Mol. Biol.* 296:833-849 (2000); Rader et al., *Proc. Natl. Acad. Sci. U.S.A.* 95:8910-8915 (1998); Barbas et al., *J. Am. Chem. Soc.* 116:2161-2162 (1994); Barbas et al., *Proc. Natl. Acad. Sci. U.S.A.* 92:2529-2533 (1995); Ditzel et al., *J. Immunol.* 157: 739-749 (1996); Berezov et al., *BIAjournal* 8:Scientific Review 8 (2001); Igarashi et al., *J. Biochem (Tokyo)* 117: 452-7 (1995); Bourgeois et al., *J. Virol* 72:807-10 (1998); Levi et al., *Proc. Natl. Acad. Sci. U.S.A.* 90:4374-8 (1993); Polymenis and Stoller, *J. Immunol.* 152:5218-5329 (1994) and Xu and Davis, *Immunity* 13:37-45 (2000). See also, U.S. Pat. Nos. 6,951,646; 6,914,128; 6,090,382; 6,818,216; 6,156, 313; 6,827,925; 5,833,943; 5,762,905 and 5,760,185. Each of these references is hereby incorporated by reference in its entirety.

Accordingly, in one embodiment, the invention provides antibodies comprising one or more heavy and/or light chain CDR3 domains from the particular antibody described herein, wherein the antibody is capable of specifically binding to misfolded human PrP. Preferably, such antibodies (a) are capable of competing for binding with; (b) retain the functional characteristics; (c) bind to the same epitope; and/or (d) have a similar binding affinity as the particular antibodies described herein. In another embodiment, the antibodies of the invention may further include the CDR2 domain of the heavy and/or light chain variable region of the particular antibodies described herein, or of another PrP antibody, wherein the antibody is capable of specifically binding to misfolded human PrP. In another embodiment, the antibodies of the invention further may include the CDR1 of the heavy and/or light chain variable region of the particular antibodies described herein, or the CDR1 of the heavy and/or light chain variable region of another misfolded human PrP antibody, wherein the antibody is capable of specifically binding to misfolded human PrP.

To permit their use as cytotoxins per se, to inhibit directly the growth or proliferation of misfolded PrP+ disease cells presenting the MDEYSNQNN (SEQ ID No. 14) epitope, the antibodies can exert their anti-cancer activity through endogenous mechanisms such as complement-mediated cytotoxicity (CDC) and/or antibody-dependent cellular cytotoxicity (ADCC). It will be appreciated that the antibodies can be engineered or selected to have altered effector function, to enhance effectiveness in treating cancer.

Cysteine residues, for instance, may be introduced to the Fc region to allow interchain disulfide bond formation. The resulting homodimeric antibody may have improved internalization capacity, and more importantly may have increased complement dependent cytotoxicity (CDC) and/or ADCC activities. Homodimeric antibodies with enhanced anti-tumour activity may also be prepared using heterobifunctional cross-linkers as described in Wolff et al, Cancer Research 53:2560-2565 (1993). Alternatively, an antibody can be engineered which has dual Fc regions and enhanced CDC and ADCC activity.

Particularly suitable acceptor antibodies are antibodies already known to have PrP binding affinity. Such donor antibodies are most desirably of human origin, but they can also derive from acceptor antibodies of non-human origin, including mouse, rat, rabbit, goat, sheep, primate and the like. It will be appreciated that human antibody acceptor sequences different from those exemplified herein can be identified and used to accommodate the presently desired CDRs. This is achieved by modeling the structure of a preferred antibody using for instance the Swiss-Model [http://swissmodel.expasy.org/repository] or similar software and selecting, from among the numerous human antibody sequences available in public databases, a human acceptor antibody sequence that, with CDR sequences altered as herein preferred, approximates the same structural conformation as the preferred antibodies. In embodiments, the acceptor antibodies, and the resulting present antibodies, are of the IgG1 isotype, but they may also be IgG2 or IgG4. Moreover, the isotype of the antibody, as dictated by the constant region, can be manipulated to alter or eliminate the effector function of the resulting antibody. That is, the constant region of the present antibodies is either wild type human antibody constant region, or a variant thereof that incorporates amino acid modifications, i.e., amino acid additions, substitutions or deletions that alter the effector function of the constant region, such as to enhance serum half-life, reduce or enhance complement fixation, reduce or enhance antigen-dependent cellular cytotoxicity and improve antibody stability. The number of amino acid modifications in the constant region is usually not more than 20, such as 1-10 e.g., 1-5 modifications, including conservative amino acid substitutions.

In embodiments, the half-life of the antibody is improved by incorporating one or more amino acid modifications, usually in the form of amino acid substitutions, for instance at residue 252, e.g., to introduce Thr, at residue 254, e.g., to introduce Ser, and/or at residue 256 e.g., to introduce Phe. Still other modifications can be made to improve half-life, such as by altering the CH1 or CL region to introduce a salvage receptor motif, such as that found in the two loops of a CH2 domain of an Fc region of an IgG. Such alterations are described for instance in U.S. Pat. No. 5,869,046 and U.S. Pat. No. 6,121,022.

Altered C1q binding, or reduced complement dependent cytotoxicity, can be introduced by altering constant region amino acids at locations 329, 331 and 322, as described in U.S. Pat. No. 6,194,551. The ability of the antibody to fix complement can further be altered by introducing substitutions at positions 231 and 239 of the constant region, as described in WO94/029351.

The framework regions of the light and heavy chains of the present antibodies and fragments also desirably have the sequence of a human antibody variable region, but incorporating the CDRs herein specified. In embodiments, the heavy chain variable region is human IgG4 in origin, which is generally considered to be inert for effector function. In specific embodiments, the heavy chain variable region is that of human IgG, such as the human IgG1 antibody variant having the sequence designated Genbank gi 2414502. Alternatively, the heavy chain variable region is that of human IgG4 antibody species designated Genbank gi 2414502.

The framework regions of the heavy and light chains of the present antibodies may also incorporate amino acid modifications, i.e., amino acid deletions, additions or substitutions, which further improve upon the properties of the antibody or fragment, in accordance with techniques established for antibody humanization. Such framework modifications can be modeled on the framework regions of antibody sequences provided in public databases, and on framework regions of antibodies known to bind PrP, such as those antibodies referenced in the background section hereof. Preferred framework substitutions are those which yield antibodies having a greater preference for binding misfolded PrP associated with disease cells.

Framework modifications can also be made to reduce immunogenicity of the antibody or to reduce or remove T cell epitopes that reside therein, as described for instance by Carr et al in US2003/0153043.

Antibodies of the invention can also be altered in the variable region to eliminate one or more glycosylation sites, and/or to improve physical stability of the antibody. For example, in one embodiment, the physical stability of the antibody is improved by substituting the serine at position 228 of the variable region with a proline residue (i.e., the antibody has a variable region comprising a S228P mutation). The S228P alteration significantly stabilizes the antibody structure against the formation of intrachain disulfide bonds. In another embodiment, the variable region is altered to eliminate one or more glycosylation sites resident in the variable region. More particularly, it is desirable in the sequence of the present antibodies to eliminate sites prone to glycosylation. This is achieved by altering the occurrence of one or more N-X-(S/T) sequences that occur in the parent variable region (where X is any amino acid residue), particularly by substituting the N residue and/or the S or T residue.

Antibodies of the invention can be engineered to include a variety of constant regions. In one embodiment, the antibody comprises a constant region the sequence of which corresponds to the constant region of an antibody of human origin, such as a human IgG1 constant region. In a particular embodiment, the constant region is inert for effector function (e.g., essentially devoid of effector function). In a specific embodiment the constant region is a human IgG4 constant region.

In accordance with embodiments of the present invention, the heavy and light chain variable regions comprise a heavy chain variable region of SEQ ID No. 8, and/or a light chain variable region having SEQ ID No. 7, as follows:

Light chain variable region (VL):

[SEQ ID No. 7]
MDTRAPTQLLGLLLLWLPGATFAQVLTQTPSPVSAAVGGTVTINCQSSQS

LYNKNWLSWYQKKPGQPPKLLIYKASTLESGVSSRFKGSGSGTQFTLTIS

GVQCDDAATYYCQGEFSCSSADCTAFGGGTEVVV

Heavy chain variable region (VH):

[SEQ ID No. 8]
METGLRWLLLVAVLKGVQCQSVEESGGHLVTPGTPLTLTCTVSGIDLSTY

AMGWVRQAPGKGLEWIGVITKSGNTYYASWAKGRFAISKTSTTVDLKITS

PTTEDTATYFCGRYGIGVSYYDIWGPGTLVTVSSGQ

Thus, the antibody may be of any useful class, including IgA, IgD, IgE, IgG and IgM, and of any isotype including IgG1, IgG2, IgG3, and IgG4. Preferred antibodies are IgG1. In more specific and preferred embodiments, the entire light and heavy chains of the intact antibody are set out below as SEQ ID Nos. 9 and 10, respectively:

Entire Light chain:

[SEQ ID NO. 9]
MDTRAPTQLLGLLLLWLPGATFAQVLTQTPSPVSAAVGGTVTINCQSSQS

LYNKNWLSWYQKKPGQPPKLLIYKASTLESGVSSRFKGSGSGTQFTLTIS

GVQCDDAATYYCQGEFSCSSADCTAFGGGTEVVVKGDPVAPTVLIFPPAA

DQVATGTVTIVCVANKYFPDVTVTWEVDGTTQTTGIENSKTPQNSADCTY

NLSSTLTLTSTQYNSHKEYTCKVTQGTTSVVQSFNRGDC;

Entire Heavy chain:

[SEQ ID No. 10]
METGLRWLLLVAVLKGVQCQSVEESGGHLVTPGTPLTLTCTVSGIDLSTY

AMGWVRQAPGKGLEWIGVITKSGNTYYASWAKGRFAISKTSTTVDLKITS

PTTEDTATYFCGRYGIGVSYYDIWGPGTLVTVSSGQPKAPSVFPLAPCCG

DTPSSTVTLGCLVKGYLPEPVTVTWNSGTLTNGVRTFPSVRQSSGLYSLS

SVVSVTSSSQPVTCNVAHPATNTKVDKTVAPSTCSKPTCPPPELLGGPSV

FIFPPKPKDTLMISRTPEVTCVVVDVSQDDPEVQFTWYINNEQVRTARPP

LREQQFNSTIRVVSTLPIAHQDWLRGKEEKCKVHNKALPAPIEKTISKAR

GQPLEPKVYTMGPPREELSSRSVSLTCMINGFYPSDISVEWEKNGKAEDN

YKTTPAVLDSDGSYFLYSKLSVPTSEWQRGDVFTCSVMHEALHNHYTQKS

ISRSPGK;

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072. Moreover, the binding sites on human IgG1 for FcγRI, FcγRII, FcγRIII and FcRn have been mapped and variants with improved binding have been described (see Shields et al. (2001) J. Biol. Chem. 276: 6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

Antibodies of the present disclosure can contain one or more glycosylation sites in either the light or heavy chain variable region. Such glycosylation sites may result in increased immunogenicity of the antibody or an alteration of the pK of the antibody due to altered antigen binding (Marshall et al (1972) *Annu Rev Biochem* 41:673-702; Gala and Morrison (2004) *J Immunol* 172:5489-94; Wallick et al (1988) *J Exp Med* 168:1099-109; Spiro (2002) *Glycobiology* 12:43R-56R; Parekh et al (1985) *Nature* 316:452-7; Mimura et al. (2000) *Mol Immunol* 37:697-706). Glycosylation has been known to occur at motifs containing an N—X—S/T sequence. In some instances, it is preferred to have an antibody that does not contain variable region glycosylation. This can be achieved either by selecting antibodies that do not contain the glycosylation motif in the variable region or by mutating residues within the glycosylation region.

For example, aglycoslated antibodies can be made (i.e., which lack glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, the antibody can have an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 ($\alpha$(1,6)-fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 and Yamane-Ohnuki et al. (2004) *Biotechnol Bioeng* 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the $\alpha$-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al. (2002) *J. Biol. Chem.* 277:26733-26740). Antibodies with a modified glycosylation profile can also be produced in chicken eggs, as described in PCT Publication WO 06/089231. Alternatively, antibodies with a modified glycosylation profile can be produced in plant cells, such as *Lemna*. Methods for production of antibodies in a plant system are disclosed in the U.S. Patent application corresponding to Alston & Bird LLP attorney docket No. 040989/314911, filed on Aug. 11, 2006. PCT Publication WO 99/54342 describes cell lines engineered to express glycoprotein-modifying glycosyl transferases (e.g., $\beta$(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180). Alternatively, the fucose residues of the antibody can be cleaved off using a fucosidase enzyme; e.g., the fucosidase $\alpha$-L-fucosidase removes fucosyl residues from antibodies (Tarentino et al. (1975) *Biochem.* 14:5516-23).

In addition, the antibody can be pegylated, for example, to increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See, e.g., EP 0 154 316 and EP 0 401 384.

Thus, the present invention includes antibodies that comprise the CDR sequences first recited above, and otherwise can be chimeric, humanized, human or otherwise engineered antibodies.

The antibodies and binding fragments are useful both for diagnostic purposes, including in vivo imaging to identify endogenous sites of misfolded PrP, and for sample testing to detect misfolded PrP as a soluble protein or as a cell-borne surface protein. The antibodies and binding fragments are also useful for therapeutic purposes to treat diseases in which misfolded PrP is implicated.

For either purpose, the antibody or binding fragment can be conjugated to an appropriate agent, to form an immunoconjugate. Agents appropriate for treating disease include cytotoxic agents or toxins that include chemotherapeutics and radiotherapeutics. For diagnostic purposes, appropriate agents are detectable labels that include radioisotopes or fluorescent markers for whole body imaging, and radioisotopes, enzymes, fluorescent labels and the like for sample testing. In these diagnostic approaches, the agent can serve as a label either directly, as such, or indirectly as an agent that will bind a desired label such as a labeled secondary antibody that binds the agent.

For diagnostics, the detectable labels can be any of the various types used currently in the field of in vitro diagnostics, including particulate labels including biotin/streptavidin, metal sols such as colloidal gold, radioactive isotopes such as $I^{125}$ or $Tc^{99}$ presented for instance with a peptidic chelating agent of the $N_2S_2$, $N_3S$ or $N_4$ type, chromophores including fluorescent markers such as FITC and PE, luminescent markers, phosphorescent markers and the like, as well as enzyme labels that convert a given substrate to a detectable marker, and polynucleotide tags that are revealed following amplification such as by polymerase chain reaction. Suitable enzyme labels include horseradish peroxidase, alkaline phosphatase and the like. For instance, the label can be the enzyme alkaline phosphatase, detected by measuring the presence or formation of chemiluminescence following conversion of 1,2 dioxetane substrates such as adamantyl methoxy phosphoryloxy phenyl dioxetane (AMPPD), disodium 3-(4-(methoxyspiro{1,2-dioxetane-3,2'-(5'-chloro)tricyclo{3.3.1.13,7}decan}-4-yl)phenyl phosphate (CSPD), as well as CDP and CDP-star® or other luminescent substrates well-known to those in the art, for example the chelates of suitable lanthanides such as Terbium(III) and Europium(III). The detection means is determined by the chosen label. Appearance of the label or its reaction products can be achieved using the naked eye, in the case where the label is particulate or chromatic and accumulates at appropriate levels, or using instruments such as a spectrophotometer, a luminometer, a fluorimeter, and the like, all in accordance with standard practice.

Likewise, imaging agents may be included in the composition or in additional compositions. Suitable imaging agents include commercially available agents used in positron emission tomography (PET), computer assisted tomography (CAT), single photon emission computerized tomography, x-ray, fluoroscopy, and magnetic resonance imaging (MRI).

Imaging agents useful with the antibody to screen for endogenous cancer sites or for misfolded PrP in plaque or other forms include metals, radioactive isotopes and radioopaque agents (e.g., gallium, technetium, indium, strontium, iodine, barium, bromine and phosphorus-containing compounds), radiolucent agents, contrast agents, dyes (e.g., fluorescent dyes and chromophores) and enzymes that catalyze a colorimetric or fluorometric reaction. In general, such agents may be attached or entrapped using a variety of techniques as described above, and may be present in any orientation. See, e.g., U.S. Pat. Nos. 6,159,443 and 6,391,280, both of which are expressly incorporated by reference herein.

Contrast agents according to the present invention are useful in the imaging modalities, such as X-ray contrast agents, light imaging probes, spin labels or radioactive units. Examples of suitable materials for use as contrast agents in MRI include the gadolinium chelates currently available, such as diethylene triamine pentaacetic acid (DTPA) and gadopentotate dimeglumine, as well as iron, magnesium, manganese, copper, and chromium. Examples of materials useful for CAT and x-rays include iodine based materials, such as ionic monomers typified by diatrizoate and iothalamate, non-ionic monomers such as iopamidol, isohexol, and ioversol, non-ionic dimers, such as iotrol and iodixanol, and ionic dimers, for example, ioxagalte.

Preferred agents for use with PET scan include $N^{13}$ and fluorodeoxyglucose (FDG).

For therapy, a cytotoxin can be conjugated with the antibody or binding fragment through non-covalent interaction, but more desirably, by covalent linkage either directly or, more preferably, through a suitable linker. In a preferred embodiment, the conjugate comprises a cytotoxin and an antibody or any binding fragment thereof. Immunoconjugates of the antibody and cytotoxin are made using a variety of bifunctional protein coupling agents such as N-succinimidyl-3-(2-pyridyldithiol)propionate, iminothiolane, bifunctional derivatives of imidoesters such as dimethyl adipimidate HCl, active esters such as disuccinimidyl suberate, aldehydes such as glutaraldehyde, bis-azido compounds such as bis-(p-diazoniumbenzoyl)-ethylenediamine), diisocyanates such as toluene 2,6-diisocyanate, and bis-active fluorine compounds (such as 1,5-difluoro-2,4-dinitrobenzene). $C^{14}$-labeled 1-isothiocyanobenzyl-3-methyldiethylene triamine-pentaacetic acid (MX-DTPA) is a chelating agent suitable for conjugation of radionuclide to the antibody. One particularly useful linker is succinimidyl-(4-iodoacetyl)aminobenzoate (SIAB) which is a mid-length crosslinker for amine-to-sulfhydryl conjugation via N-hydroxysuccinimide ester and iodoacetyl reactive groups.

The cytotoxin component of the immunoconjugate can be any agent that is cytotoxic to the cells targeted by the antibody such as a chemotherapeutic agent, a toxin such as an enzymatically active toxin of bacterial, fungal, plant or animal origin, or fragments thereof, or a small molecule toxin, or a radioactive isotope such as $^{212}Bi$, $^{131}I$, $^{131}In$, $^{111}In$, $^{90}Y$ and $^{186}Re$, or any other agent that acts to inhibit the growth or proliferation of a target disease cell.

Chemotherapeutic agents useful in such immunoconjugates include maytansinoids such as DM-1 and DM-4, adriamycin, doxorubicin, epirubicin, 5-fluoroouracil, cytosine arabinoside ("Ara-C"), cyclophosphamide, thiotepa, busulfan, cytoxin, taxanes, e.g. paclitaxel, and docetaxel, taxotere, methotrexate, cisplatin, melphalan, vinblastine, bleomycin, etoposide, ifosamide, mitomycin C, mitoxantrone, vincristine, vinorelbine, carboplatin, teniposide, daunomycin, carminomycin, aminopterin, dactinomycin, mitomycins, esperamicins, 5-FU, 6-thioguanine, 6-mercaptopurine, actinomycin D, VP-16, chlorambucil, melphalan, and other related nitrogen mustards. Also useful are hormonal agents that act to regulate or inhibit hormone action on tumors such as tamoxifen and onapristone. Toxins and fragments thereof which can be used include diphtheria A chain, nonbonding active fragments of diphtheria toxin, cholera toxin, botulinus toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, sapaonaria, officinalis inhibitor, gelonin, saporin, mitogellin, restrictocin, phenomycin, enomycin, and the tricothcenes. Small molecule toxins include, for example, calicheamicins, palytoxin and CC1065. Also useful are the taxanes including taxol and paclitaxel.

In one particular aspect, the present invention provides immunoconjugates that incorporate urease, as a cytotoxic component, conjugated with at least one antigen binding site of the antibody herein characterized. The incorporation of urease as the cytotoxic component of an immunoconjugate has been described in the literature (see U.S. Pat. No. 7,211,250 and U.S. Pat. No. 7,264,800 both to Helix BioPharma Corporation, and both incorporated herein by reference in their entirety). While urease itself is not cytotoxic, its cytotoxicity arises from its ability to convert urea to pH elevating compounds such as ammonia. Thus, the urease-based immunoconjugate may raise the pH of interstitial fluid to which the cancer cells are exposed, by addition of urease to the interstitial fluid in the subject. Urease can convert the substrate urea to ammonia and carbamate. This enzymatic activity may increase the pH making the environment more basic. The environment around a cancer cell is typically acidic (Webb, S. D., et al. (2001) Novartis Found Symp. 240:169-81). Thus, by raising the pH of the extracellular environment in this manner, growth of the cancer cell is inhibited. Accordingly, addition of the immunoconjugate in certain embodiments of the invention causes the pH of the interstitial fluid, and particularly that surrounding misfolded PrP+ disease cells, to be raised by at least 0.1 pH unit, e.g., 0.1-0.5 pH units or greater.

As used herein, the term "urease" refers to an enzyme having the enzymatic activity of a urea amidohydrolase (E.C. 3.5.1.5). Urease also includes proteins comprising the entire urease, subunits, or fragments thereof, and/or urease with amino acid substitutions, deletions or additions that preserve the urea amidohydrolase activity of the polypeptide. A truncated urease sequence as used herein is a fragment of urease that is free from a portion of the intact urease sequence beginning at either the amino or carboxy terminus of urease. Methods for isolating native urease and for identifying active fragments and modified urease polypeptides are given below.

In embodiments of the invention, the urease is jack bean urease having SEQ ID No. 13, as shown below:

```
                                              (SEQ ID No. 13)
MKLSPREVEKLGLHNAGYLAQKRLARGVRLNYTEAVALIASQIM

EYARDGEKTVAQLMCLGQHLLGRRQVLPAVPHLLNAVQVEATFP

DGTKLVTVHDPISRENGELQEALFGSLLPVPSLDKFAETKEDNR

IPGEILCEDECLTLNIGRKAVILKVTSKGDRPIQVGSHYHFIEV

NPYLTFDRRKAYGMRLNIAAGTAVRFEPGDCKSVTLVSIEGNKV

IRGGNAIADGPVNETNLEAAMHAVRSKGFGHEEEKDASEGFTKE

DPNCPFNTFIHRKEYANKYGPTTGDKIRLGDTNLLAEIEKDYAL

YGDECVFGGGKVIRDGMGQSCGHPPAISLDTVITNAVIIDYTGI

IKADIGIKDGLIASIGKAGNPDIMNGVFSNMIIGANTEVIAGEG

LIVTAGAIDCHVHYICPQLVYEAISSGITTLVGGGTGPAAGTRA

TTCTPSPTQMRLMLQSTDDLPLNFGFTGKGSSSKPDELHEIIKA

GAMGLKLHEDWGSTPAAIDNCLTIAEHHDIQINIHTDTLNEAGF

VEHSIAAFKGRTIHTYHSEGAGGGHAPDIIKVCGIKNVLPSSTN

PTRPLTSNTIDEHLDMLMVCHHLDREIPEDLAFAHSRIRKKTIA

AEDVLNDIGAISIISSDSQAMGRVGEVISRTWQTADKMKAQTGP

LKCDSSDNDNFRIRRYIAKYTINPAIANGFSQYVGSVEVGKLAD

LVMWKPSFFGTKPEMVIKGGMVAWADIGDPNASIPTPEPVKMRP

MYGTLGKAGGALSIAFVSKAALDQRVNVLYGLNKRVEAVSNVRK

LTKLDMKLNDALPEITVDPESYTVKADGKLLCVSEATTVPLSRN

YFLF
```

Alternatively, the urease may be of any origin, including, e.g., bacteria, plants, fungi and viruses. A number of studies have provided detailed information about the genetics of ureases from a variety of evolutionarily diverse bacteria, plants, fungi and viruses (Mobley, H. L. T. et al. (1995) Microbiol. Rev. 59: 451-480; Eur. J. Biochem., 175, 151-165 (1988); Labigne, A. (1990) International publication No. WO 90/04030; Clayton, C. L. et al. (1990) Nucleic Acid Res. 18, 362; and U.S. Pat. Nos. 6,248,330 and 5,298,399, each of which is incorporated herein by reference). Of particular interest is urease that is found in plants (Sirko, A. and Brodzik, R. (2000) Acta Biochim Pol 47(4):1189-95). One exemplary plant urease is jack bean urease.

The amino acid sequences of other useful urease sequences are available in public databases, e.g., Entrez (www.ncbi.nlm.nih.gov/Entrez/). Additionally, primers that are useful for amplifying ureases from a wide variety of organisms may be utilized by employing the CODEHOP (COnsensus-DEgenerate Hybrid Oligonucleotide Primer) as described in Rose, et al. (1998) Nucl. Acids Res. 26:1628.

Thus useful forms of urease include the naturally occurring forms as well as functionally active variants thereof. Two general types of amino acid sequence variants are contemplated. Amino acid sequence variants are those having one or more substitutions in specific amino acids which do not destroy the urease activity. These variants include silent variants and conservatively modified variants which are substantially homologous and functionally equivalent to the native protein. A variant of a native protein is "substantially homologous" to the native protein when at least about 80%, more preferably at least about 90%, even more preferably at least about 95%, yet even more preferably 98%, and most preferably at least about 99% of its amino acid sequence is identical to the amino acid sequence of the native protein. A variant may differ by as few as 1 or up to 10 or more amino acids.

A second type of variant includes size variants of urease which are isolated active fragments of urease. Size variants may be formed by, e.g., fragmenting urease, by chemical modification, by proteolytic enzyme digestion, or by combinations thereof. Additionally, genetic engineering techniques, as well as methods of synthesizing polypeptides directly from amino acid residues, can be employed to produce size variants.

By "functionally equivalent" is intended that the sequence of the urease variant defines a chain that produces a protein having substantially the same biological activity as the native urease. Such functionally equivalent variants that comprise substantial sequence variations are also encompassed by the invention. Thus, a functionally equivalent variant of the native urease protein will have a sufficient biological activity to be therapeutically useful. Methods are available in the art for determining functional equivalence. Biological activity can be measured using assays specifically designed for measuring activity of the native urease protein, as exemplified herein.

Because of the degeneracy of the genetic code, a multitude of nucleic acid sequences encoding urease may be produced, some of which may bear minimal sequence homology to known urease nucleic acid sequences. Such "silent variations" are one species of "conservatively modified variations", discussed below. The invention embraces any possible codon variation of nucleic acid sequences encoding a polypeptide with urease activity. As well, urease polypeptides include one or more conservatively modified variations (or simply "conservative variations") of the sequences of known urease polypeptide sequences. Such conservative variations comprise substitutions, additions or deletions that alter, add or delete a single amino acid or a small percentage of amino acids. One of ordinary skill in the art will recognize that an individual substitution, deletion, or addition that substitutes, deletes, or adds a single amino acid or a small percentage of amino acids (typically less than 5%, more typically less than 4%, 2%, 1%, or less) in a sequence typically constitutes conservative variations where such changes result in the deletion of an amino acid, addition of an amino acid, or substitution of an amino acid with a chemically similar amino acid.

The urease protein sequences, including conservatively substituted sequences, can be present as part of larger polypeptide sequences such as occur upon the addition of one or more domains for purification of the protein (e.g., poly his segments, FLAG tag segments, etc.), e.g., where the additional functional domains have little or no effect on the activity of the urease protein portion of the immunoconjugate, or where the additional domains can be removed by post synthesis processing steps, such as by treatment with a protease.

The active agents may be joined together in any order to form the immunoconjugate. Thus, where the urease may be joined to either the amino or carboxy termini of the targeting antibody. The antibody may also be joined to an internal region of the urease, or conversely, the urease may be joined to an internal location of the antibody, as long as the attachment does not interfere with the respective activities of the molecules.

The targeting antibody and the urease may be attached by any of a number of means well known to those of skill in the art. Typically, the active agent is conjugated, either directly or through a linker (spacer), to the antibody. However, where both the antibody and the urease are entirely genetically encoded, it may be preferable to recombinantly express the chimeric molecule as a fusion protein.

The procedure for attaching an agent to an antibody or other polypeptide targeting molecule will vary according to the chemical structure of the agent. Polypeptides typically contain a variety of functional groups; e.g., carboxylic acid (COOH) or free amine (—NH2) groups, which are available for reaction with a suitable functional group on a urease to bind the antibody thereto.

Alternatively, the antibody and/or urease may be derivatized to expose or attach additional reactive functional groups. The derivatization may involve attachment of any of a number of linker molecules. The linker is capable of forming covalent bonds to both the antibody and the urease. Suitable linkers include those first mentioned above, and particularly straight or branched-chain carbon linkers, heterocyclic carbon linkers, or peptide linkers. The linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

A bifunctional linker having one functional group reactive with a group on a particular agent, and another group reactive with an antibody, may be used to form the desired immunoconjugate. Alternatively, derivatization may involve chemical treatment of the targeting moiety, e.g., glycol cleavage of the sugar moiety of the glycoprotein antibody with periodate to generate free aldehyde groups. The free aldehyde groups on the antibody may be reacted with free amine or hydrazine groups on an agent to bind the urease thereto. (see U.S. Pat. No. 4,671,958). Procedures for generation of free sulfhydryl groups on polypeptide, such as antibodies or antibody fragments, are also known (see U.S. Pat. No. 4,659,839).

Immunoconjugates of the antibody and urease can be made using a variety of bifunctional protein coupling agents such as N-succinimidyl-3-(2-pyridyldithiol)propionate, iminothiolane, bifunctional derivatives of imidoesters such as dimethyl adipimidate HCl, active esters such as disuccinimidyl suberate, aldehydes such as glutaraldehyde, bis-azido compounds such as bis-(p-diazoniumbenzoyl)-ethylenediamine), diisocyanates such as toluene 2,6-diisocyanate, and bis-active fluorine compounds (such as 1,5-difluoro-2,4-dinitrobenzene).

In some circumstances, it is desirable to liberate the urease from the antibody when the conjugate has reached its target site. Therefore, conjugates comprising linkages which are cleavable in the vicinity of the target site may be used. Cleaving of the linkage may be prompted by enzymatic activity or conditions to which the conjugate is subjected either inside the target cell or in the environment of the target site. It should be appreciated that when the target site is a tumor, a linker which is cleavable under conditions present at the tumor site (e.g. when exposed to tumor-associated enzymes or acidic pH) may be used. Useful linkers that are pH sensitive are described, for instance, in WO 86/001409, WO 94/020487, WO 2009/158668 and WO 2010/053596, incorporated herein by reference.

A number of other useful cleavable linkers are known to those of skill in the art (see U.S. Pat. Nos. 4,618,492; 4,542,225, and 4,625,014.) The mechanisms for release of an active agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system.

The immunoconjugate thus can be produced by chemically conjugating the antibody and the urease. In the alternative, the immunoconjugate can be made recombinantly, provided its components are all genetically encoded. Generally, this involves creating a DNA sequences that encodes the immunoconjugate, placing the DNA in an expression cassette under the control of a particular promoter, expressing the protein in a host, isolating the expressed protein and, if required, renaturing the protein.

DNA encoding the immunoconjugate, as a fusion protein, may be prepared by any suitable method, including, for example, cloning and restriction of appropriate sequences or direct chemical synthesis by methods such as the phosphotriester method of Narang et al. (1979) Meth. Enzymol. 68: 90-99; the phosphodiester method of Brown et al. (1979) Meth. Enzymol. 68: 109-151; the diethylphosphoramidite method of Beaucage et al. (1981) Tetra. Lett., 22: 1859-1862; and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. Alternatively, subsequences can be cloned and the appropriate subsequences cleaved using appropriate restriction enzymes. The fragments can then be ligated to produce the desired DNA sequence.

While the two molecules are preferably essentially directly joined together, the molecules may be separated by a peptide spacer consisting of one or more amino acids. Generally the spacer will have no specific biological activity other than to join the proteins or to preserve some minimum distance or other spatial relationship between them. However, the constituent amino acids of the spacer may be selected to influence some property of the molecule, such as the folding, net charge, or hydrophobicity.

The nucleic acid sequences encoding the fusion protein, consisting of an antibody light chain and a separate antibody heavy chain, at least one such chain incorporating a terminal urease, may be expressed in a variety of host cells that secrete the expression product, including E. coli, other bacterial hosts, yeast, and various higher eukaryotic cells such as the COS, CHO and HeLa cells lines and myeloma cell lines. The recombinant protein gene will be operably linked to appropriate expression control sequences for each host. For E. coli this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for E. coli and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed and secreted, the recombinant fusion proteins can be purified according to standard procedures of the art, including ammonium sulfate precipitation, affinity columns, column chromatography, gel electrophoresis and the like (see, R. Scopes (1982) Protein Purification, Springer-Verlag, N.Y.; Deutscher (1990) Methods in Enzymology Vol.

182: Guide to Protein Purification., Academic Press, Inc. N.Y.). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

According to one embodiment of the invention, the cancer cells are contacted with an imaging agent before or after, or both before and after being contacted with the active agent. For example, after urease has been targeted to the tumor cells, it may have the ability to modulate or regulate the tumor external environment, e.g., through pH changes. Imaging agents that favor a basic environment will then be more efficacious.

Both luminescent cyclen-based lanthamide chelates and those primarily yielding magnetic resonance signatures have been shown to be sensitive to changes in pH. Luminescent probes used for sensing pH changes typically detect changes in the fluorescence lifetime of the lanthamide ion as a function of pH. Analogously, magnetic resonance contrast agents which modulate the water proton relaxivity via changes in pH are useful in the instant invention. In both cases, by changing the pH in a given system, one can envision agents with enhanced contrast.

Accordingly, a pH sensitive contrast agent is utilized at or near the cancer cell. The cancer cell or cells are also exposed to a urease composition containing urease enzyme to cause a change in pH at or near the cancer cell. In this way, a change in pH causes the nuclear magnetic resonance relaxation properties of water protons or other nuclei in the aqueous medium to be changed in a manner that is reflective of pH. Examples of pH sensitive contrast agents that may be utilized include those agents that contain a lanthamide metal, such as Ce, Pr, Nd, Sm, Eu, Gd, Db, Dy, Ho, Er, Tm, Yb, and the like, or another paramagnetic element, such as Fe, Mn, 17O, or the like. Specific contrast agents that may be utilized include H(2)(17)0, GdDOTA-4AmP(5−) which is described in Magn Reson Med. 2003 February;49(2):249-57, and Fe(III)meso-tetra(4-sulfonatophenyl)porphine (Fe-TPPS4) as described in Helpern et al. (1987) Magnetic Resonance in Medicine 5:302-305 and U.S. Pat. No. 6,307,372, which is incorporated herein by reference. In addition, Gd based with polyion, as described in Mikawa et al. Acad. Radiol (2002) 9(suppl 1):S109-S1111, may be used in the invention.

As another alternative, a shift reagent may be provided in the aqueous medium surrounding the cancer cell. The shift reagent is configured such that a change in pH affects the chemical shift properties of the water protons or other nuclei in a manner that is reflective of pH. The change in chemical shift properties may then be measured using nuclear magnetic resonance to determine whether the active agent is biologically active.

Exemplary shift reagents that may be used include those containing a lanthamide metal, such as Ce, Pr, Nd, Sm, Eu, Gd, Db, Dy, Ho, Er, Tm, or Yb, or another paramagnetic element. Examples of specific shift reagents that may be utilized include Tm(DOTP) (5−), the thulium (III) complex of 1,4,7,10-tetraazacyclododecane-N,N',N",N'"-tetra(methylenephosphate). Dy(PPP) (2)(7)-dysprosium tripolyphosphate, and the like.

In one embodiment of the invention, a dual-contrast-agent strategy using two gadolinium agents, such as the pH-insensitive GdDOTP(5−) and the pH-sensitive GdDOTA-4AmP (5−), may be utilized to generate pH maps by MRI, as described in Magn Reson Med (2003) February; 49(2):249-57.

Antibody Compositions

Therapeutic formulations of the antibody, binding fragment or the conjugate are prepared for storage by mixing the antibody or conjugate having the desired degree of purity with optional pharmaceutically acceptable carriers, excipients or stabilizers (Remington's Pharmaceutical Sciences, 16$^{th}$ edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl, or benzyl alcohol; alkyl parabens such as methyl or propyl paraben; catechol; resorcinol; cyclohexanol; 3-pentanol; and m-cresol); low molecular weight (less than about 10 residues) polypeptides; proteins such as serum, albumin, gelatin, or immunoglobulins; hydrophilic polymers such as polyvinylpyrrolidone; amino acids such as glycine, glutamine, asparagine, histidine, arginine or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, PLURONICS or polyethylene glycol (PEG).

The active ingredients to be used for in vivo administration will be sterile. This is readily accomplished by filtration through sterile filtration membranes.

Diagnostically useful compositions comprising the antibody will incorporate a carrier suitable for diagnostic purposes, such as a solution of saline or buffered saline including phosphate buffered saline, together with any desired stabilizers or preservatives. Of course, the composition can be provided in a lyophilized form to prolong storage stability.

Dosing and Administration

The antibody, binding fragment or immunoconjugate may be administered with a physiologically tolerable, e.g., pharmaceutically-acceptable, diluent, carrier, or excipient, in unit dosage form, and as part of an overall treatment regimen adapted for treatment or diagnosis of a particular medical condition, or for imaging a subject for diagnostic purposes.

Any appropriate route of administration can be employed, for example, parenteral, intravenous, subcutaneous, intramuscular, intracranial, intraorbital, ophthalmic, intraventricular, intracapsular, intraspinal, intracisternal, intraperitoneal, intranasal, aerosol, or oral administration. Preferably, the antibody is administered parenterally, either by infusion or injection.

The antibody, and its binding fragments and conjugates, are useful in the treatment and detection of diseases and conditions that are associated with misfolded PrP. It will thus be appreciated that an effective amount of the antibody, fragment or immunoconjugate is an amount effective alone or as part of a treatment regimen that retards or inhibits the growth or proliferation of disease cells presenting with a misfolded form of PrP in which the MDEYSNQNN (SEQ ID No. 14) epitope is antibody-accessible.

The antibody is useful particularly in the treatment of a variety of cancers, to inhibit the growth or proliferation of cancer cells (i.e., to deplete cancer cells) and tumours comprising them, including hematopoietic cell cancers and solid tumours. Conditions or disorders to be treated include benign or malignant tumors (e.g., renal, liver, kidney, bladder, breast, gastric, ovarian, colorectal, prostate, pancreatic, lung, vulva, and thyroid); hepatic carcinomas; sarcomas; glioblastomas;

and various head and neck tumors; leukemias and lymphoid malignancies. Tumour cells that can usefully be treated with the present antibody, binding fragment or conjugate are identifiable as cells that bind the present antibody. In particular embodiments, the cancer cells are misfolded PrP-presenting cancer cells that include ovarian cancer cells and lymphoid cancer cells.

The types of ovarian cancer that can be treated with the present antibodies, fragments or conjugates include those within the three major categories, according to the kind of cells from which they were formed, i.e., (1) epithelial tumors that arise from cells that line or cover the ovaries; (2) germ cell tumors that originate from cells that are destined to form eggs within the ovaries; and (3) sex cord-stromal cell tumors that begin in the connective cells that hold the ovaries together and produce female hormones. Also included are tumors that are adjacent to ovarian tissues, such as extraovarian peritoneal carcinoma (intraperitoneal carcinomatosis).

The common epithelial tumors begin in the surface epithelium of the ovaries and account for about 90% of all ovarian cancers. They are divided into a number of subtypes—including serous, endometrioid, mucinous, and clear cell tumors—that can be further classified as benign (noncancerous) or malignant (cancerous) tumors. Serous tumors are the most widespread forms of ovarian cancer. They account for 40% of common epithelial tumors. About 50% of these tumors are malignant, 33% are benign, and 17% are of borderline malignancy. Serous tumors occur most often in women who are between 40 and 60 years of age. Endometrioid tumors represent approximately 20% of common epithelial tumors. In about 20% of individuals, these cancers are associated with endometrial carcinoma (cancer of the womb lining). In 5% of cases, they also are linked with endometriosis, an abnormal occurrence of endometrium (womb lining tissue) within the pelvic cavity. About 80% of these tumors are malignant, and the remainder usually is of borderline malignancy. Endometrioid tumors occur primarily in women who are between 50 and 70 years of age. Mucinous tumors make up about 1% of all common epithelial tumors. Most (approximately 80%) of these tumors are benign, 15% are of borderline malignancy, and only 5% are malignant. Mucinous tumors appear most often in women between 30 to 50 years of age. Clear cell tumors account for about 6% of common epithelial tumors. Nearly all of these tumors are malignant. Approximately one-half of all clear cell tumors are associated with endometriosis. Most patients with clear cell tumors are between 40 and 80 years of age.

Also treatable with the present antibodies, fragments or conjugates are the rare types of ovarian tumours, such as Brenner tumors, undifferentiated tumors, and transitional cell tumors as well as germ cell tumours that are formed from egg-making cells within the ovaries.

The antibody, and its binding fragments and conjugates, are useful also in the treatment and detection of the prion diseases, including particularly Creutsfeldt Jacob Disease (CJD). Particularly well suited are those antibodies that direct clearance of aggregated PrP upon binding thereto. Such antibodies include those recognized by macrophages. Dosage sizes and dosing regimens that are effective for this purpose are those that reduce the presence of PrP aggregates, as determined by any method useful therein, such as whole body imaging or in vitro screening using any agent that binds selectively to misfolded PrP.

For use as an anti-cancer agent, the appropriate dosage will depend on the particular type of disease to be treated, as defined above, the severity and course of the disease, whether the agent is administered for preventative or therapeutic purposes, previous therapy, the patients clinical history and response to the agent, and the discretion of the attending physician. The agent is suitably administered to the patient at one time or over a series of treatments.

For example, depending on the type and severity of the disease, about 1 µg/kg to 15 mg/kg (e.g., 0.1-20 mg/kg) of antibody or conjugate is a candidate dosage for administration to the patient, whether, for example, by one or more separate administrations, or by continuous infusion. A typical daily dosage is in the range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. Unit doses can be in the range, for instance of about 5 mg to 500 mg, such as 50 mg, 100 mg, 150 mg, 200 mg, 250 mg and 300 mg. The progress of anti-cancer therapy is monitored by conventional techniques and assays.

In embodiments, the present antibodies can be administered by intravenous infusion, such as at an initial dose of 4 mg/kg over 90 minutes, then 2 mg/kg over 30 minutes, once weekly for 52 weeks, with follow up as required.

When the urease-based immunoconjugate is used, additional guidance is available for the treatment of target cells including cancer cells that are misfolded PrP+. As discussed above, urease catalyzes the hydrolysis of urea, leading to the production of carbamate and ammonia. In an aqueous environment, the carbamate rapidly and spontaneously decomposes to yield a second molecule of ammonia and one of carbon dioxide. Urease has a wide variety of functions. Its primary environmental role is to allow organisms to use external and internally generated urea as a nitrogen source. In plants urease may participate in the systemic nitrogen transport pathways and possibly act as a toxic defense protein.

The substrate for urease is urea, which is produced in the liver, carried in the bloodstream to the kidneys, and excreted in urine. Serum concentrations of urea in healthy humans are typically between one and 10 mM, but urea levels in urine may exceed 0.5 M (Merck Manual of Diagnosis and Therapy, Merck and Co., Inc., Rahway, N.J., 1999). Urea is also present in the secretions of the major and minor exocrine glands at concentrations approximately equivalent to serum, so a large proportion of circulating urea is translocated onto cell surfaces by secretory systems, or in tissue exudates (Burne, R. A., and Chen, Y. M., Microbes and Infection, 2, 2000; 533-542). For example, adult humans secrete almost 1 liter of saliva per day containing 1-10 mM urea, and approximately 20-25% of all urea produced enters the intestinal tract rather than exiting the body in urine (Visek, W. J., Fed. Proc. 31 (1972) 1178-1193). There is no apparent active efflux mechanism for exocrine secretion of urea, so it is believed that the uncharged urea molecule simply follows water through the cells and tight junctions of the epithelium. As a consequence, the surfaces of cells in the human body are bathed in a fluid which contains urea (McLean R. J. C., et al. CRC, Crit. Rev. Microbiol. 16 (1988) 37-79).

For the urease-based immunoconjugate, any effective administration regimen regulating the timing and sequence of doses may be used. Exemplary dosage levels for a human subject will depend on the mode of administration, extent (size and distribution) of the tumor, patient size, and responsiveness of the cancer to urease treatment.

Where a urease composition is injected directly into a tumor, an exemplary dose is 0.1 to 1,000 international units urease activity per mm3 tumor. For example, and assuming a relatively uniform distribution of the urease in the tumor is achieved, a dose of between 0.5 and 5 international units may be suitable. The placement of the injection needle may be guided by conventional image guidance techniques, e.g., fluoroscopy, so that the physician can view the position of the needle with respect to the target tissue. Such guidance tools can include ultrasound, fluoroscopy, CT or MRI.

The effectiveness or distribution of the administered urease conjugate dose may be monitored, during or after direct injection of urease into the tumor, by monitoring the tumor tissue by a tool capable of detecting changes in pH within the cancerous tissue region of the subject. Such tools may include a pH probe that can be inserted directly into the tumor, or a visualization tool, such as magnetic resonance imaging (MRI), computerized tomography (CT), or fluoroscopy. MRI interrogation may be carried out in the absence of additional imaging agents, based simply on differences in magnetic properties of tissue as a function of pH. CT or fluoroscopic imaging may require an additional pH-sensitive imaging agent whose opacity is affected by the pH of the tissue medium. Such agents are well known to those of skill in the art.

Before any urease conjugate injection, the tumor tissue can be visualized by its lower pH relative to surrounding normal tissue. Thus, the normal tissue may have a normal pH of about 7.2, whereas the tumor tissue may be 0.1 to 0.4 or more pH units lower. That is, before any urease is injected, the extent of tumor tissue can be defined by its lower pH. Following urease conjugate administration, the pH of the tumor region having urease will begin to rise, and can be identified by comparing the resulting images with the earlier pre-dosing images.

By interrogating the tissue in this manner, the degree of change in pH and extent of tissue affected may be monitored. Based on this interrogation, the physician may administer additional composition to the site, and/or may administer composition at additional areas within the tumor site. This procedure may be repeated until a desired degree of pH changes, e.g., 0.2 to 0.4 pH units, has been achieved over the entire region of solid tumor.

Dosing by direct injection may be repeated by suitable intervals, e.g., every week or twice weekly, until a desired end point, preferably substantial or complete regression of tumor mass is observed. The treatment efficacy can be monitored, as above, by visualizing changes in the pH of the treated tissue during the course of treatment. Thus, before each additional injection, the pH of the tissue can be visualized to determine the present existing extent of tumor, after which changes in the pH of the tissue can be used to monitor the administration of the new dose of urease composition to the tissue.

Where the urease conjugate is administered parenterally by a method other than direct injection, an exemplary dose of the urease is 100-100,000 international units/kg urease activity/kg subject body weight.

As noted above, imaging techniques that are sensitive to changes in tissue pH, may be used to monitor the effectiveness of the dose administered. Since such targeting may take several hours or more, the method may involve monitoring tumor pH, as above, before urease conjugate injection, and several hours, e.g., 12-24 hours following dosing, to confirm that the tumor site has been adequately dosed, as evidenced by rise in pH of the tumor region. Depending on the results of this interrogation, the method may dictate additional dosing until a desired rise in pH, e.g., 0.2-0.4 pH units, is observed. Once this dose is established, the patient may be treated with a similar dose of the urease composition on a regular basis, e.g., one or twice weekly, until a change in tumor size or condition is achieved.

The frequency of dosing will depend on the pharmacokinetic parameters of the agent and the route of administration. Dosage and administration are adjusted to provide sufficient levels of the active agent or to maintain the desired effect. Accordingly, the pharmaceutical compositions can be administered in a single dose, multiple discrete doses, continuous infusion, sustained release depots, or combinations thereof, as required to maintain a desired minimum level of the agent.

Pharmaceutical Combinations

The antibody, or a binding fragment or conjugate, can be administered to a subject in need thereof in combination with useful other agents. Administration "in combination with" one or more further therapeutic agents includes simultaneous (concurrent) and consecutive administration in any order. Other therapeutic regimens may be combined with the administration of the anti-cancer agents, e.g., antibodies or conjugates, of the instant invention. For example, the patient to be treated with such anti-cancer agents may also receive radiation therapy, such as external beam radiation. Alternatively, or in addition, a chemotherapeutic agent may be administered to the patient. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992). The chemotherapeutic agent may precede, or follow administration or the anti-tumor agent, e.g., antibody, or may be given simultaneously therewith. The antibody may be combined with any of the toxins described above with reference to the conjugates, or any other suitable drug particularly include irinotecan (CPT-11), cisplatin, cyclophosphamide, melphalan, dacarbazine, doxorubicin, daunorubicin, and topotecan, as well as tyrosine kinase inhibitors.

Particularly for use in treating ovarian cancer, the present antibody, binding fragment or immunoconjugate can be administered in combination with a taxane such as paclitaxel and/or carboplatin, or any other drug in use for ovarian cancer treatment.

It may be desirable to administer also antibodies or conjugates against other tumor associated antigens or their ligands, such as antibodies or agents that also target the same type of disease cell as targeted by the present antibody. Thus, the present antibodies are usefully administered in combination with agents already in use for the treatment of liquid tumours including particularly leukemias and lymphomas, as well as solid tumours including ovarian tissue tumours.

Thus, in embodiments, the present antibody, a binding fragment thereof or an immunoconjugate based thereon can be used in combination with a chemotherapeutic agent that enhances binding of the antibody. It has been determined, for instance, that ovarian cancer cells incubated with paclitaxel display increased antibody binding. Thus, in one embodiment, the present invention comprises a treatment method in which a subject presenting with an ovarian cancer, including one having a misfolded PrP phenotype, is first treated with paclitaxel, and is then treated with the antibody, fragment or immunoconjugate of the present invention. Alternatively, the subject can receive the drugs simultaneously. Other anti-cancer agents that also cause an increase in antibody binding can be identified using the same in vitro methodology as exemplified herein. It is anticipated that taxanes other than paclitaxel, such as taxol, will be similarly useful, for instance.

In the present method, the urease-based immunoconjugate is administered for instance to a solid tumor, in an amount effective for the urease to raise the extracellular pH of the tumor fluid by at least 0.1 pH unit, e.g., 0.1 to 0.5 pH units or more. In certain embodiments, the extracellular pH of the fluid is raised to at least pH 7.0, 7.2, or higher.

The urease conjugate may be administered directly into the subject's tumor or parenterally other than by direct injection. Also as described above, the change in pH produced by the administration of urease conjugate may be monitored by determining changes in pH in tumor tissue and the extent of those changes, using imaging tools for visualizing tumor pH, or by direct pH measurements of the tumor.

Kits

In another embodiment of the invention, an article of manufacture containing materials useful for the diagnosis or treatment of the disorders described herein is provided. The article of manufacture comprises the present antibody, or binding fragment or immunoconjugate thereof, in a container and suitably bearing a label. Suitable containers include, for example, bottles, vials, syringes, and test tubes. The containers may be formed from a variety of materials such as glass or plastic. The container holds a composition which is effective for detecting or treating the condition and may have a sterile access port (for example the container may be an intravenous solution bag or vial having a stopper pierceable by a hypodermic injection needle). The label on or associated with, the container indicates that the composition is used for treating a cancer condition or for treating a transmissible spongiform encephalopathy, such as CJD. The article of manufacture may further compromise a second container compromising a pharmaceutically-acceptable buffer, such as phosphate-buffered saline, Ringer's solution and dextrose solution. It may further include other matters desirable from a commercial and use standpoint, including other buffers, diluents, filters, needles, syringes, and package inserts with instructions for use in accordance with the present invention. Control agents or standards useful in the method can also be included in the kit, such as a PrP preparation standard.

As noted antibodies as described herein may be used in a pharmaceutical composition for the treatment, prophylaxis or amelioration of a prion-misfolding associated disease or disorder in a subject. Such conditions particularly include the transmissible spongiform encephalopathies that afflict humans, such as CJD. A pharmaceutical composition comprising a therapeutically effective amount of an antibody according to some embodiments of the invention and a pharmaceutically acceptable excipient may be administered to a subject to treat the prion-misfolding associated disease or disorder. The antibody may inhibit the formation of PrPSc aggregates, or block the further conversion of PrPC to PrPSc isoforms. The pharmaceutical composition may be useful, for example, in reducing a neurotoxic effect of PrPSc formation and/or aggregation. The pharmaceutical composition may further comprise an additive or agent that increases the permeability of the blood-brain barrier (for administration into the blood). In the alternative, the composition can be administered directly into the cerebrospinal fluid. Progression of disease can be monitored by administering the present antibody in complex with an imaging agent thereby to reveal the location and/or extent of PrP aggregation, as discussed further below.

It will be appreciated that the present antibody can be used to treat all subjects who could benefit from the present method include mammals including humans as well as livestock, and pets provided of course that these subjects produce PrP in a misfolded form that retains immunoreactivity for the present PrP antibodies.

Detection and Diagnosis

Antibodies and fragments thereof that bind selectively to the target epitope are used, in accordance with an aspect of the invention, to screen cancer or other cells to detect those which present misfolded PrP. In a preferred embodiment, screening is applied to a sample of cancer cells taken from a subject that is a candidate for PrP antibody therapy. Subjects testing positive for cancer cells that present the misfolded form of PrP can then be scheduled for therapy with the present antibody or fragment, or an immunoconjugate thereof. Standard techniques, combined with the antibodies or other binding agents herein described can be used to screen cancer cells. Desirably, the antibodies incorporate a detectable label. The label may be detectable by itself. (e.g., radio-isotope labels or fluorescent labels) or, in the case of an enzymatic label, may catalyze chemical alteration of a substrate compound or composition which is detectable. Radionuclides that can serve as detectable labels include, for example, I-131, I-123, I-125, Y-90, Re-188, Re-186, At-211, Cu-67, Bi-212, and Pd-109.

In situ detection of the binding to cancer cells bearing misfolded PrP can also be performed using the present antibody or fragment, by immunofluorescence or immunoelectron microscopy. For this purpose, a histological specimen is removed from the patient, and a labeled form of the present antibody is applied to it, preferably by overlaying the antibody on a biological sample, in keeping with standard immunohistochemistry techniques. This procedure also allows for distribution of the PrP antigen to be examined within biopsied tumour tissue, to reveal only those sites at which PrP is presented in misfolded form. It will be apparent for those skilled in the art that a wide variety of histological methods are readily available for in situ detection.

More particularly, misfolded PrP antibodies or binding fragments of the present invention may be used to monitor the presence or absence of antibody reactivity in a biological sample, e.g., a tissue biopsy from brain, skin, liver, heart, kidney, pancreas, bowel, spleen, muscle, fat, skin, ovary and the like, from a cell, or from fluid such as cerebrospinal fluid, blood including plasma, urine, seminal fluid, and the like, using standard detection assays. Immunological assays may involve direct detection, and are particularly suited for screening large amounts of samples for the presence of cancer cells that present misfolded PrP. For example, antibodies may be used in any standard immunoassay format (e.g., ELISA, Western blot, immunoprecipitation, flow cytometry or RIA assay) to measure complex formation. Any appropriate label which may be directly or indirectly visualized may be utilized in these detection assays including, without limitation, any radioactive, fluorescent, chromogenic (e.g., alkaline phosphatase or horseradish peroxidase), or chemiluminescent label, or hapten (for example, digoxigenin or biotin) which may be visualized using a labeled, hapten-specific antibody or other binding partner (e.g., avidin). Exemplary immunoassays are described, e.g., in Ausubel et al., supra, Harlow and Lane, Antibodies: A Laboratory Approach, Cold Spring Harbor Laboratory, New York (1988), and Moynagh and Schimmel, Nature 400:105, 1999. For example, using the antibodies described herein, misfolded PrP is readily detected at the cell surface using standard flow cytometry methods. Samples found to contain labeled complex compared to appropriate control samples are taken as indicating the presence of misfolded PrP, and are thus indicative of a cancer or other disease amenable to treatment with the present antibodies.

When the urease-based conjugate is used, the subject can be interrogated with a diagnostic tool capable of detecting changes in extracellular pH in a subject's tissue, as described above. The diagnostic tool is preferably a pH-sensitive diagnostic agent, such as an imaging, contrast or shift reagent, as described above, capable of localizing in the tumor that may be administered prior to, following or concurrently with the active agent. A tissue region is identified within the subject that shows an elevation in extracellular pH following the administration. Any tool capable of identifying the diagnostic agent may be used to detect the agent, such as MRI, PET scan, and the like as described above.

In one embodiment, the method includes administering urease conjugate to the subject employed in an anti-tumor therapy, and the identification is used for detecting the localization of urease in a solid tumor. The identifying may be used for monitoring the change in size and shape of the tumor in response to urease conjugate administration.

In one embodiment employing PET scan, the subject is administered 13N-labelled ammonia. The patient is then administered urease conjugate in an amount effective to reach the tumor site. The urease hydrolyzes urea to produce non-labelled ammonia. Over time, the labelled ammonia is diluted or displaced, causing a gradual clearing on the scan. In another embodiment employing PET scan, the subject is administered 13N-labelled urea. The patient is then administered urease conjugate in an amount effective to reach the tumor site. The urease hydrolyzes the labelled urea to produce labelled ammonia, which could be detected on the scan.

The present antibody is produced suitably by recombinant DNA means, as exemplified herein. For production, there is provided a DNA molecule that encodes the heavy chain of the present antibody, and a DNA molecule that encodes the light chain thereof. The DNA further encodes any suitable signal peptide suitable for expression of a secretable chain precursor that enables proper externalization with folding and disulfide formation to elaborate the desired antibody as a secreted, dimerized and processed protein. To this end, the present invention provides, in one embodiment, a polynucleotide comprising a sequence that encodes the light chain variable region of a preferred antibody, as set out in SEQ ID No. 7. Also provided, in another embodiment, is a polynucleotide comprising a sequence that encodes the heavy chain variable region of a preferred antibody, as set out in SEQ ID No. 8.

In more specific embodiments, the present invention provides a polynucleotide that encodes the entire light chain (SEQ ID No. 9) and a polynucleotide that encodes the entire heavy chain (SEQ ID No. 10) of the presently preferred antibody, as recited below:

Heavy chain

```
DNA Fragment with HindIII at 5'end and
NotI at 3'end
                                          [SEQ ID No. 11)
ATGGAGACTGGGCTGCGCTGGCTTCTCCTGGTCGCTGTGCTCAA

AGGTGTCCAGTGTCAGTCGGTGGAGGAGTCCGGGGGTCACCTGG

TCACGCCTGGGACACCCCTGACACTCACCTGCACAGTCTCTGGA

ATCGACCTCAGTACCTATGCAATGGGCTGGGTCCGCCAGGCTCC

AGGGAAGGGGCTGGAGTGGATCGGAGTCATTACTAAAAGTGGTA

ACACATACTACGCGAGCTGGGCGAAAGGCCGATTCGCCATCTCC

AAAACCTCGACCACGGTGGATCTAAAGATCACCAGTCCGACAAC

CGAGGACACGGCCACCTATTTCTGTGGCAGATATGGTATTGGTG

TTTCTTACTATGACATCTGGGGCCCAGGCACTCTGGTCACCGTC

TCCTCA

GGCCAACCTAAGGCTCCATCAGTCTTCCCACTGGCCCCCTGCTG

CGGGGACACACCCAGCTCCACGGTGACCCTGGGCTGCCTGGTCA
```

AAGGGTACCTCCCGGAGCCAGTGACCGTGACCTGGAACTCGGGC

ACCCTCACCAATGGGGTACGCACCTTCCCGTCCGTCCGGCAGTC

CTCAGGCCTCTACTCGCTGAGCAGCGTGGTGAGCGTGACCTCAA

GCAGCCAGCCCGTCACCTGCAACGTGGCCCACCCAGCCACCAAC

ACCAAAGTGGACAAGACCGTTGCGCCCTCGACATGCAGCAAGCC

CACGTGCCCACCCCCTGAACTCCTGGGGGGACCGTCTGTCTTCA

TCTTCCCCCCAAAACCCAAGGACACCCTCATGATCTCACGCACC

CCCGAGGTCACATGCGTGGTGGTGGACGTGAGCCAGGATGACCC

CGAGGTGCAGTTCACATGGTACATAAACAACGAGCAGGTGCGCA

CCGCCCGGCCGCCGCTACGGGAGCAGCAGTTCAACAGCACGATC

CGCGTGGTCAGCACCCTCCCCATCGCGCACCAGGACTGGCTGAG

GGGCAAGGAGTTCAAGTGCAAAGTCCACAACAAGGCACTCCCGG

CCCCCATCGAGAAAACCATCTCCAAAGCCAGAGGGCAGCCCCTG

GAGCCGAAGGTCTACACCATGGGCCCTCCCCGGGAGGAGCTGAG

CAGCAGGTCGGTCAGCCTGACCTGCATGATCAACGGCTTCTACC

CTTCCGACATCTCGGTGGAGTGGGAGAAGAACGGGAAGGCAGAG

GACAACTACAAGACCACGCCGGCCGTGCTGGACAGCGACGGCTC

CTACTTCCTCTACAGCAAGCTCTCAGTGCCCACGAGTGAGTGGC

AGCGGGGCGACGTCTTCACCTGCTCCGTGATGCACGAGGCCTTG

CACAACCACTACACGCAGAAGTCCATCTCCCGCTCTCCGGGTAA

ATGA

Light Chain:

```
DNA Fragment with HindIII at 5'end and
NotI at 3'end
                                          [SEQ ID No. 12]
ATGGACACGAGGGCCCCCACTCAGCTGCTGGGGCTCCTGCTGCT

CTGGCTCCCAGGTGCCACATTTGCCCAAGTGCTGACCCAGACTC

CATCCCCTGTGTCTGCAGCTGTGGGAGGCACAGTCACCATCAAT

TGCCAGTCCAGTCAGAGTCTTTATAATAAGAACTGGTTATCCTG

GTATCAGAAGAAACCAGGGCAGCCTCCTAAGCTCCTGATCTACA

AGGCATCCACTCTGGAATCTGGGGTCTCATCGCGGTTCAAGGGC

AGTGGATCTGGGACACAGTTCACTCTCACCATCAGCGGCGTGCA

GTGTGACGATGCTGCCACTTACTACTGTCAAGGCGAATTTAGTT

GTAGTAGTGCTGATTGTACGGCTTTCGGCGGAGGGACCGAGGTG

GTGGTCAAA

GGTGATCCAGTTGCACCTACTGTCCTCATCTTCCCACCAGCTGC

TGATCAGGTGGCAACTGGAACAGTCACCATCGTGTGTGTGGCGA

ATAAATACTTTCCCGATGTCACCGTCACCTGGGAGGTGGATGGC

ACCACCCAAACAACTGGCATCGAGAACAGTAAAACACCGCAGAA

TTCTGCAGATTGTACCTACAACCTCAGCAGCACTCTGACACTGA

CCAGCACACAGTACAACAGCCACAAAGAGTACACCTGCAAGGTG
```

-continued

ACCCAGGGCACGACCTCAGTCGTCCAGAGCTTCAATAGGGGTGA
CTGTTAG

It will be appreciated that polynucleotide equivalents also can be used, in which synonymous codons are replaced within the sequences provided, to produce the present antibodies.

In embodiments, there are also provided vectors that comprise polynucleotides that encode the heavy chain or the variable region thereof and that encode the light chain or the variable region thereof. To express the antibodies, the polynucleotides are incorporated operably within expression vectors, i.e. operatively linked to transcriptional and translational control sequences. Expression vectors include plasmids, retroviruses, cosmids, and the like. The expression vector and expression control sequences are chosen to be compatible with the expression host cell used. The antibody light chain gene and the antibody heavy gene can be inserted into separate vectors. In a preferred embodiment, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human CH or CL immunoglobulin sequence, with appropriate restriction sites engineered so that any VH or VL sequence can be easily inserted and expressed, as described above. In such vectors, splicing usually occurs between the splice donor site in the inserted J region, and the splice acceptor site preceding the human C region, and also at the splice regions that occur within the human CH exons. Polyadenylation and transcription termination occur at native chromosomal sites downstream of the coding regions. The recombinant expression vector can also encode a signal peptide that facilitates secretion of the antibody chain from a host cell. The antibody chain gene may be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

Polynucleotides encoding the heavy chain and/or the light chain, and vectors comprising these can be used for transformation of a suitable mammalian host cell. Methods for introduction of heterologous polynucleotides into mammalian calls include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, polynucleotides may be introduced into mammalian cells by viral vectors. Mammalian cell lines useful as hosts for expression of the antibody-encoding polynucleotides include many immortalized cell lines available from the American Type Culture Collection (ATCC). These include, inter alia, Chine hamster ovary (CHO) cells, NSO, SP2 cells, HeLa cells, baby hamster kidney (BHK) cells, monkey kidney cells (COS), human hepatocellular carcinoma cells (e.g., HepG2), A549 cells, 3T3 cells, and a number of other cell lines. In a specific embodiment, the polynucleotides are expressed in a HEK293 host. Mammalian host cells include human, mouse, rat, dog, monkey, pig, goat, bovine, horse, and hamster cells. Cell lines of particular preference are selected through determining which cell lines have high expression levels. Other cell lines that may be used are insect cell lines, such as S19 cells, amphibian cells, bacterial cells, plant cells and fungal cells. When recombinant expression vectors encoding the heavy chain or antigen-binding portion thereof are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

The antibodies of the invention can be obtained as human monoclonal antibodies. Such human monoclonal antibodies can be generated using transgenic or transchromosomic mice carrying parts of the human immune system rather than the mouse system. These transgenic and transchromosomic mice include mice referred to herein as the HuMAb Mouse® and KM Mouse®, respectively, and are collectively referred to herein as "human Ig mice."

The HuMAb Mouse® (Medarex®, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg et al. (1994), supra; reviewed in Lonberg (1994) Handbook of Experimental Pharmacology 113:49-101; Lonberg, N. and Huszar, D. (1995) Intern. Rev. Immunol. 13: 65-93, and Harding and Lonberg (1995) Ann. N.Y. Acad. Sci. 764:536-546). Preparation and use of the HuMAb Mouse®, and the genomic modifications carried by such mice, is further described in Taylor et al. (1992) Nucleic Acids Research 20:6287-6295; Chen et al. (1993) International Immunology 5: 647-656; Tuaillon et al. (1993) Proc. Natl. Acad. Sci. USA 90:3720-3724; Choi et al. (1993) Nature Genetics 4:117-123; Chen et al. (1993) EMBO J. 12: 821-830; Tuaillon et al. (1994) J. Immunol. 152:29U-2920; Taylor et al. (1994) International Immunology 6: 579-591; and Fishwild et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; 5,770,429; and 5,545,807; PCT Publication Nos. WO 92/03918; WO 93/12227; WO 94/25585; WO 97/13852; WO 98/24884; WO 99/45962 and WO 01/14424, the contents of which are incorporated herein by reference in their entirety.

In another embodiment, the human antibodies are raised using a mouse that carries human immunoglobulin sequences on transgenes and transchomosomes, such as a mouse that carries a human heavy chain transgene and a human light chain transchromosome. This mouse is referred to herein as a "KM mouse®," and is described in detail in PCT Publication WO 02/43478. A modified form of this mouse, which further comprises a homozygous disruption of the endogenous Fcγ RIIB receptor gene, is also described in PCT Publication WO 02/43478 and referred to herein as a "KM/FCGR2D mouse®." In addition, mice with either the HCo7 or HCo12 heavy chain transgenes or both can be used.

Additional transgenic animal embodiments include the Xenomouse (Abgenix, Inc., U.S. Pat. Nos. 5,939,598; 6,075, 181; 6,114,598; 6,150,584 and 6,162,963). Further embodiments include "TC mice" (Tomizuka et al. (2000) Proc. Natl. Acad. Sci. USA 97:722-727) and cows carrying human heavy and light chain transchromosomes (Kuroiwa et al. (2002) Nature Biotechnology 20:889-894; PCT Publication WO 02/092812). The contents of these patents and publications are specifically incorporated herein by reference in their entirety.

Human monoclonal antibodies also can be prepared using SCID mice into which human immune cells have been reconstituted such that a human antibody response can be generated upon immunization. See, e.g., U.S. Pat. Nos. 5,476,996 and 5,698,767, the contents of which are incorporated herein by reference in their entirety.

Antibodies of the invention also can be produced in a host cell transfectoma using, for example, a combination of recombinant DNA techniques and gene transfection methods as is well known in the art (e.g., Morrison, S. (1985) Science 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody chain genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences can be used, such as the ubiquitin promoter or $\alpha$-globin promoter. Still further, regulatory elements composed of sequences from different sources, such as the SRα promoter system, which contains sequences from the SV40 early promoter and the long terminal repeat of human T cell leukemia virus type 1 (Takebe et al. (1988) Mol. Cell. Biol. 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the invention can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because mammalian cells are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) J. Mol. Biol. 159:601-621), NSO myeloma cells, COS cells, HEK293 cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

It is likely that antibodies expressed by different cell lines or in transgenic animals will have different glycosylation from each other. However, all antibodies encoded by the polynucleotides provided herein, or comprising the amino acid sequences provided herein are part of this invention.

Embodiments are now described in the following examples.

EXAMPLES

The cell lines NCI-H929, HL-60, K562, Z138, OVCAR-3 and Du145 were obtained from the American Type Culture Collection. The cell lines C33A, SKOV-3, ES-2, NCI/ADR-Res and DoHH2 were provided by the BC Cancer Agency. Implanted tumors were provided also by the BC Cancer Agency. Peripheral blood leukocytes were prepared from fresh blood provided by normal healthy donors. Other normal primary cells were obtained from ScienCell. Anti-PrP 6H4 antibody was obtained from Prionics. NCI/ADR-Res is derived from OVCAR-8. It is an ovarian carcinoma. OVCAR-3 and SKOV-3 are ovarian adenocarcinoma. ES-2 and LTL-382 are ovarian clear cell carcinoma. LTL-409 is ovarian dysgerminoma.

Generation of Monoclonal Antibodies

Peptides comprising the sequence MDEYSNQNN (SEQ ID No. 14) were synthesized using standard methods and then coupled to carrier proteins. Prepared immunogens included both KLH-Cys-MDEYSNQNN and OVA-Cys-MDEYSNQNN.

New Zealand white rabbits were immunized subcutaneously with 0.4 mg peptide-KLH conjugates in complete Freund's adjuvant. After the initial immunization, animals were boosted several times every 2-3 weeks. The rabbit with the best titer in immunoassay was intravenously boosted with peptide antigen again, four days before the removal of the spleen. The hybridoma fusion was performed using conventional PEG cell fusion methodology. Splenocytes were harvested from the immunized rabbit and fused with rabbit plasmacytoma cells 240E-W2 (U.S. Pat. No. 5,675,063) using PEG4000 (Sigma Chemical, St. Louis, Mo.) and selected by HAT (hypoxanthine, aminopterin, and thymidine). At the end of selection hybridoma supernatants were collected and evaluated in various assays. Selected hybridomas were subsequently subcloned by limited dilution to obtain monoclonal hybridomas.

The antibody heavy and light chain genes for monoclonal ab120 were cloned from the hybridoma cells. Total RNA was extracted and reverse-transcribed to cDNA using the Qiagen TurboCapture mRNA kits. DNA fragments for L chain and the variable region (VH) of H chain of rabbit IgG were amplified by PCR with rabbit H and L chain primers. The L chain fragment was cloned into pTT5 mammalian expression vector and the VH fragment fused in-frame to the constant region of H chain pTT5 Heavy chain vector For each hybridoma clone, three plasmid DNA clones for H and L chains were sequenced and expressed as recombinant RabMAb for characterization.

Plamids encoding the IgG heavy and light chains of ab120 were isolated from transformed E. coli using EndoFree® plasmid purification kit (Qiagen). Human HEK-293-6E cells were used for transient expression of ab120 antibody. The antibody plasmids were transfected into cells at logarithmic growth phase using FreeStyle™ MAX Reagent 293 fectin (Invitrogen, Cat: 51-0031) and cultured in FreeStyle™ 293 Expression Medium (Invitrogen, Cat: 12338-18) according to manufacturer's instructions. The transfected cells were grown at 37° C. with 5% CO2 in an orbital shaker for 7 days. The antibody secreted into the culture medium was collected by spinning at 7000 rpm for 15 minutes to remove cell debris. The cleared culture supernatant was purified by protein A chromatography (HiTrap™ rProtein A FF, GE healthcare, CAT: 17-5080-01) under endotoxin free condition. Antibodies were eluted from the column in citrate elution buffer (SIGMA, CAT: C2404-100G) and adjusted to neutral pH with sodium bicarbonate buffer. The antibody preparation was concentrated and exchanged into PBS buffer. The concentration of IgG and endotoxin level in the final antibody preparation were determined by OD 280 nm quantitation and Tachypleus Amebocyte Lysate gel clot assay (Zhanjiang A&C Biological Ltd), respectively.

Monoclonal antibody ab120 was purified by protein A. Purified antibody was filter-sterilized and stored at 4C in PBS buffer (pH 7.4). The protein concentration was determined by UV absorption 280 nm) assay and PBS buffer was used a blank buffer. The final concentration is the means from triplicate readings, and was given a QC requirement of >2 mg/ml.

To measure protein purity, SDS-PAGE was performed with Bio-Rad mini electrophoresis system according to the manufacturer's instructions. The gel was then stained with Coomassie brilliant blue. The resolving gel was 12% acrylamide and the stacking gel was 4% acrylamide, with sample loading at 4 ug/lane. The assayed sample showed 2 bands (Heavy chain and Light chain) in reduced SDS-PAGE, and one band (whole IgG molecule) in non-reduced SDS-PAGE.

Endotoxin level was also assessed by the Gel Clot Tachypleus Ameboycte Lysate (TAL) kit using endotoxin standards and endotoxin-free water. Results indicated an endotoxin level of <1 EU/ml protein.

Thus in a preferred embodiment, the antibody is provided as a preparation that exhibits (a) <about 1 EU/ml protein, (b) a concentration of greater than about 2 mg/ml, (c) and migration as a single protein band when measured by non-reducing SDS-PAGE at a loading dose of 4 ug/lane and detected at 280 nm.

Anti-Peptide ELISA

Maxisorp 96-well plates were coated overnight at 2-8° C. with 100 ng/well of BSA-peptide in PBS. After blocking with PBST/casein, primary antibodies were added and incubated for 1 hour at room temperature. Rabbit antibodies were detected using goat anti-rabbit IgG-HRP and TMB substrate. After stopping the reaction with 0.25M sulfuric acid, absorbance was measured at 450 nm.

Denatured PrP ELISA

Recombinant PrP (Alicon) was mixed with LDS sample buffer (Life Technologies) and sample reducing agent (Life Technologies) and heated at 80° C. for 20 minutes. After cooling for 15 minutes, Maxisorp 96-well plates were coated with 100 ng/well of denatured PrP and incubated at 2-8° C. overnight. After blocking with PBST/BSA, primary antibodies were added and incubated for 1 hour at room temperature. Remaining steps were as described for anti-peptide ELISAs.

His-PrP Capture ELISA

Maxisorp 96-well plates were coated overnight at 2-8° C. with 100 ng/well of goat anti-His-6 antibody (QED) in PBS. After blocking with PBST/BSA, His-PrP (Alicon) was added and incubated for 1 hour at room temperature. Addition of primary antibody and remaining steps were as described for anti-peptide ELISAs.

Cell Preparation for FACS

Adherent tumor cell lines and primary cells were detached from flasks using non-enzymatic cell-dissociation buffer (Invitrogen). Peripheral blood mononuclear cells were prepared from fresh citrated blood on the day of collection using standard Ficoll centrifugation methods. Other primary cells were frozen in 10% DMSO and thawed on the day of testing. Implanted tumors were surgically removed from mice. Tumors were chopped with scissors and then treated with collagenase/hyaluronidase (Worthington Biochemical) while shaking at 37° C. for 30 minutes. Individual tumor cells were collected by passing the mixture through a 40 μm screen.

FACS

Cells with Fc receptors were treated with 10% normal human serum to block the receptors. Cells were incubated with primary antibodies for 30 minutes at 2-8° C. Following washing, cells were incubated with goat anti-rabbit AF488 for 30 minutes at 2-8° C. After the final wash, cells were incubated in 1 μg/mL propidium iodide. Cells were analyzed using either a Becton Dickinson FACSCalibur or a Becton Dickinson FACS Canto II and FCS Express Software (DeNovo Systems).

Affinity Measurements for Antibodies Binding to Peptide, Denatured PrP or Tumor Cells Binding of antibodies to peptide or denatured PrP was performed by ELISA as described above. Binding of antibodies to tumor cells was performed by FACS as described above. Antibodies were titrated to provide binding curves. EC50 values were calculated using GraphPad software.

Proteinase K Treatment of Cells

Adherent tumor cell lines were detached from flasks using non-enzymatic cell-dissociation buffer (Invitrogen). Primary cells were frozen in 10% DMSO and thawed on the day of testing. Cells were treated with proteinase K at varying concentrations for 30 minutes at 37° C. Cells were then washed and antibody binding determined by FACS, as described above.

Paclitaxel Treatment of Cells

Cells were plated in 6-well plates and allowed to adhere overnight. The following day, media was removed and replaced with fresh media containing various concentrations of paclitaxel. Cells were incubated overnight at 37C/5% $CO_2$. The following day cells were detached using non-enzymatic cell dissociation buffer, washed, and antibody binding was evaluated by FACS, as described above.

Immunoconjugate Examples

Synthesis

The immunoconjugate was formed by conjugating Ab 1c-120 with urease using SIAB (succinimidyl-(4-iodoacetyl) aminobenzoate) as linker. SIAB is a mid-length crosslinker for anime-to-sulfhydryl conjugation via N-hydroxysuccinimide (NHS) ester and iodoacetyl reactive groups. It yields a spacer arm of about 10.6 Angstroms in length. It is available commercially from Thermo Scientific, and its use in conjugation is described for instance by Hermanson, Bioconjugate Techniques, 1996, San Diego, Academic Press pp 542, 553, 568.

First, antibody 1c-120 was activated with SIAB (molar ratio SIAB:IgG=3.8:1) at the pH of the original buffer matrix, for 70 minutes. The reaction was then quenched for ten minutes at room temperature with addition of Tris-HCl buffer, to a final concentration of 5 mM. The resulting solution was chilled with ice/water, and chilled high purity urease (5 mg/ml, ~OC, GMP grade jack bean urease) was added while vortexing. Protein molar ratios were 1:2/IgG:HPU. Tris-HCl (200 mM, pH 8.45) was added at 1/10 volume to adjust the pH to 8.0-8.3, over a period of 90 minutes. For stability, hydrolyzed SIAB was added to coup most of the surface hydrosulfite of urease. The molar ratio was 1:7 (urease:hydroSIAB), room temperature, 30 minutes.

The reaction was then quenched by adding cysteine solution (100 mM in 200 mM Tris-HCl buffer, pH 8.45) to a final concentration of 5 mM, room temperature, 10 minutes. The resulting mixture was subjected to SEC separation with a GE healthcare Superose 6 10/300 column, and the fractions were collected. Fractions F10-13 minutes were pooled and dialyzed (MWCO 12-14 kD) against 20 mM arginine buffer containing 1% sucrose and 0.2 mM EDTA, pH 7.0. Collected samples were then analyzed by SDS-PAGE, by protein assay with BCA protocol, by urease-enzyme activity assay with the tube protocol, and by ELISA binding assay to reveal the immunoconjugate is active (FIGS. 9 and 10).

Results of these tests revealed the following:
Protein concentration of 0.5 mg/ml by BCA;
Urease enzyme activity of 1030 U/ml;
Urease specific activity of 2060 U/mg;
Average conjugation ratio of 2IgG/urease;
Total product: 3 mg in 6.0 ml solution
Buffer compositions: 20 nM arginine, 0.2 mM EDTA, 1% sucrose, pH 7.0

Activity Assay of Urease and Urease Conjugate

The enzymatic activity of urease or urease conjugate was carried out in a coupled enzyme reaction with glutamate dehydrogenase (GLDH). The amount of NADH oxidized was determined by measuring the change in absorbance at 340 nm (Kaltwasser, H. and Schlegel, H. G., Anal. Biochem., 16, 132, 1966). The reagents used were: 0.10 M Potassium phosphate buffer, pH 7.6; 1.80 M Urea prepared in phosphate buffer; 0.025 M Adenosine-5'-diphosphate (ADP) (10.7 mg/ml) in buffer; 0.008 M NADH (5 mg/ml) in phosphate buffer; 0.025 M α-Ketoglutarate (3.7 mg/ml) in phosphate buffer; Glutamate dehydrogenase (GLDH) solution, free from ammonium ions; 50 U/ml phosphate buffer prepared fresh prior to assay. Urease solution was prepared by dissolving in phosphate buffer to yield a concentration of 0.1-0.5 U/ml. This solution was prepared fresh prior to assay.

Assay was initiated by adding the following 2.0 mL of Phosphate buffer 2.40 ml, 0.10 ml each of urea, ADP, NADH, GLDH and α-Ketoglutarate in a cuvette. The spectrophotometer was adjusted to 340 nm and 25° C. The cuvette with the added ingredients was placed in the spectrophotometer at 25° C. for 5 minutes to attain temperature equilibration and then establish blank rate, if any, at 340 nm.

To initiate the enzymatic reaction 0.1 ml of the urease solution was added to the cuvette. The changes in the absorbance at 340 nm were recorded for 15 min. Enzyme activity was correlated with a decrease in absorbance at 340 nm per min.

In vitro Cytotoxicity Assay

Reagents were incubated with tumor cells for two hours. Cells were washed twice and then incubated with 20 mM urea for 30 minutes. Cell viability was evaluated by addition of WST-1 followed by measuring absorbance after 16-20 hours.

Preclinical Efficacy Study

ES-2 cells were grown in cell culture. On study day 0, $5 \times 10^6$ cells were implanted subcutaneously. Once tumors reached on average 100 $mm^3$, iv dosing was initiated, with 3 doses weekly. Tumor growth was monitored by measuring tumor dimensions with calipers. Tumor volumes were calculated according to the equation $L \times W^2/2$. Mice were terminated when tumors reached 800 $mm^3$, or were severely ulcerated.

Results

The ProMis™ algorithm (described in WO 2010/040209) was used to identify DSEs for human PrP. DSE3 is called the rigid loop epitope, and it is located between β-sheet 2 and α-helix 1.

Figure 1:
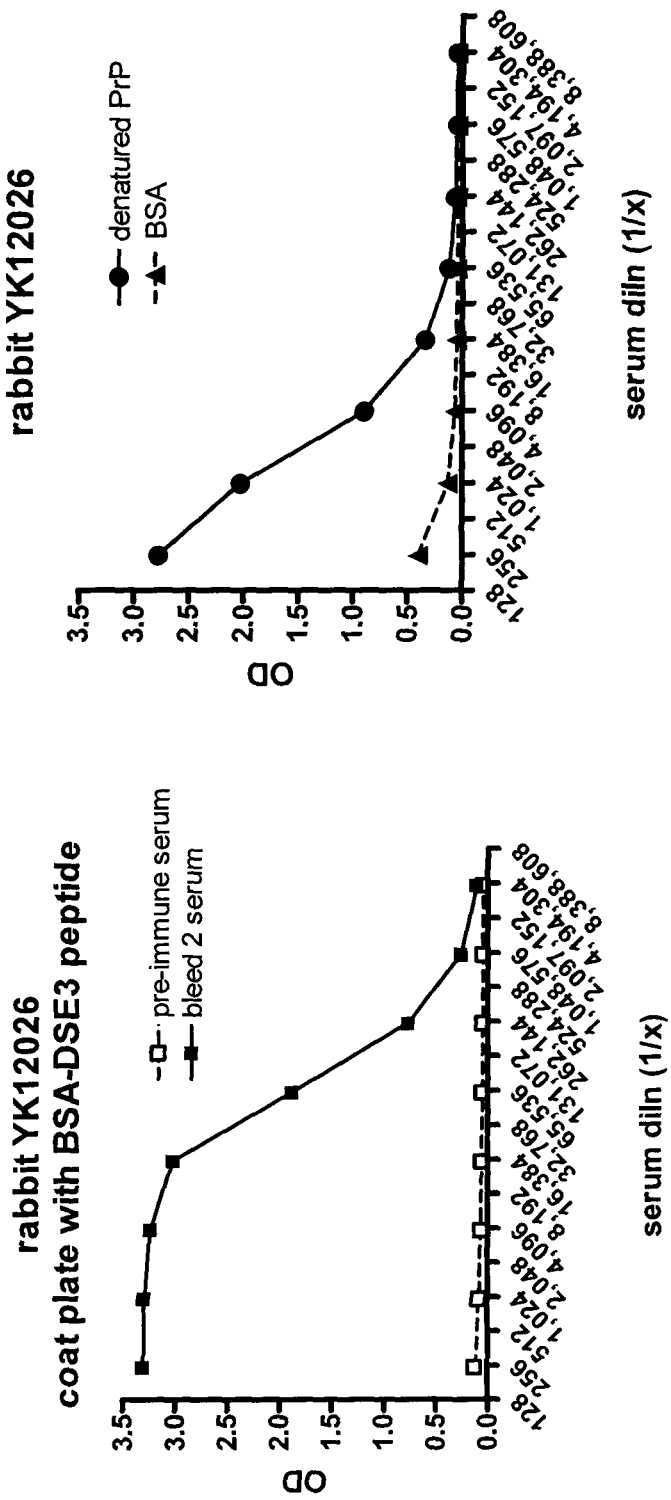

Anti-DSE3 antibodies were developed using the specific sequence MDEYSNQNN (SEQ ID No. 14), and two different immunogens, i.e., KLH-Cys-DSE3 and OVA-Cys-DSE3. Rabbits were immunized as described in the Materials and Methods and the antisera from the rabbits were evaluated. Rabbits made excellent responses to the immunogen peptides (FIG. 1a). In addition, antisera showed excellent binding to full-length denatured PrP (FIG. 1b). After performing fusions, monoclonal antibodies were generated. Seven recombinant rabbit monoclonal antibodies raised against DSE3 were then fully evaluated.

Figure 2:
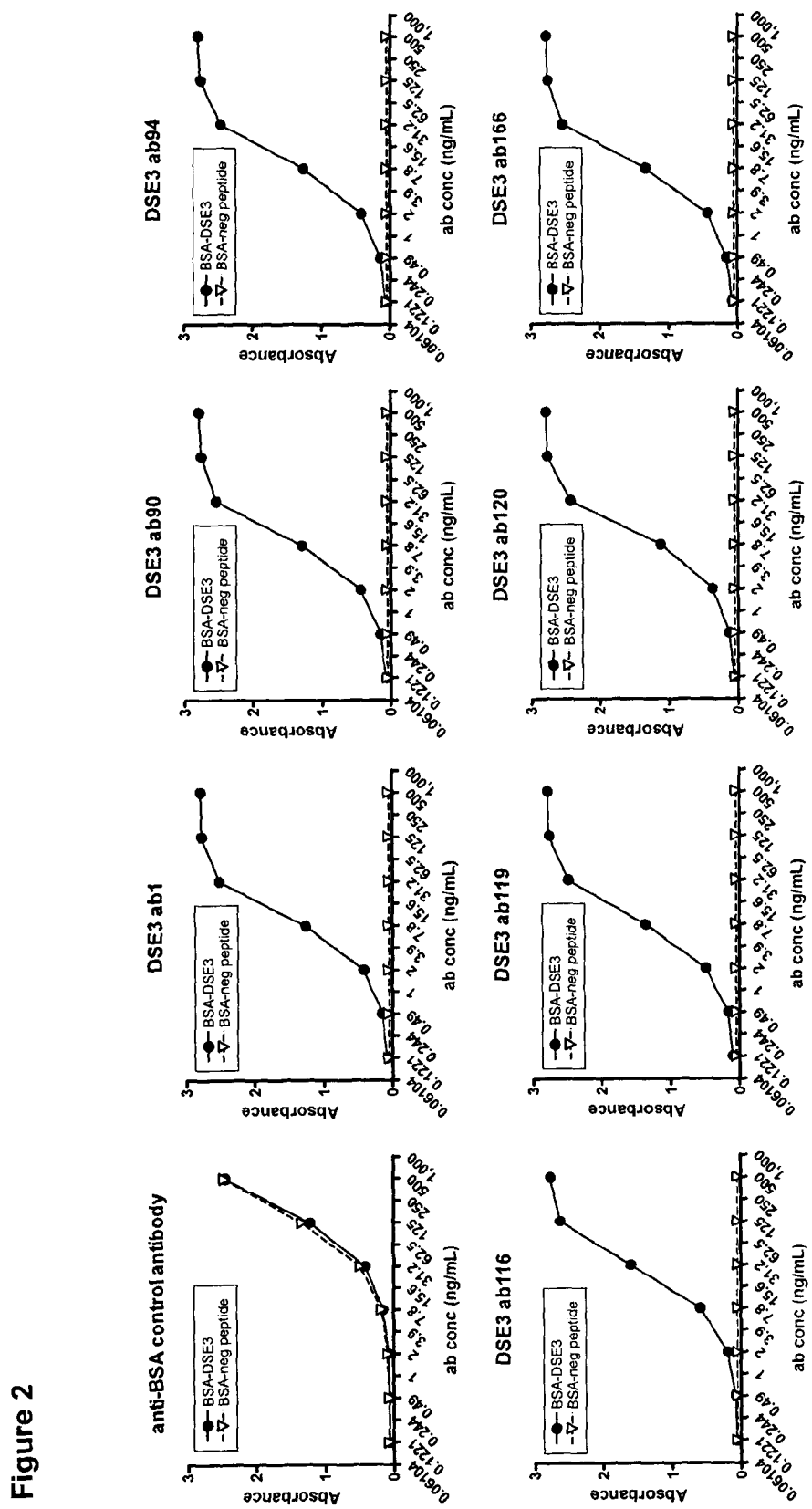

Antibodies were tested for binding to the immunogen peptides, and all seven antibodies showed excellent titers (FIG. 2). $EC_{50}$ values for peptide binding were determined by ELISA. All antibodies showed very high affinity for peptides, with $EC_{50}$s in the $10^{-11}$M range (Table 1).

Figure 3:
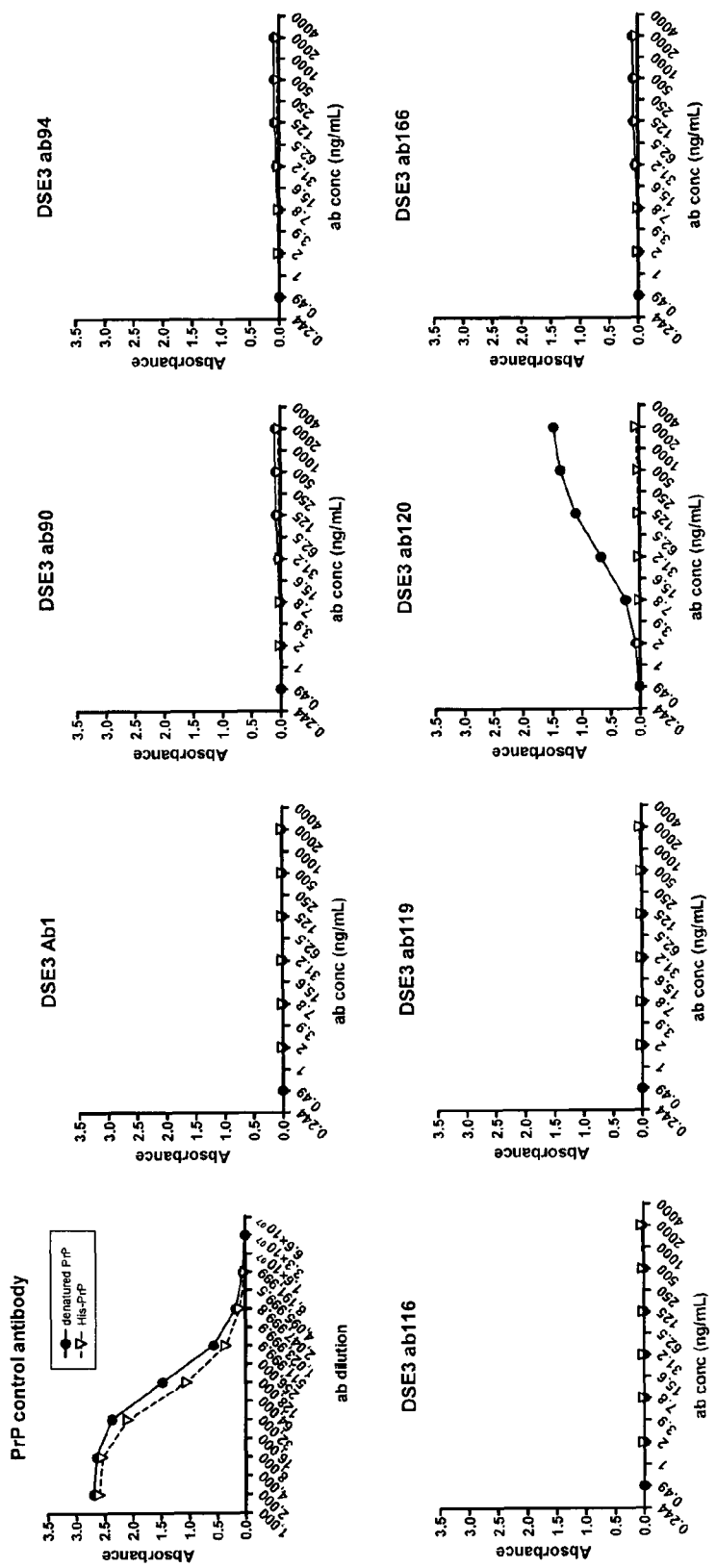

All antibodies were then tested by ELISA for binding to denatured full-length recombinant PrP (FIG. 3). One antibody exhibited a titer for denatured PrP that was similar to the anti-peptide affinities, in the $10^{-11}$ M range (Table 1). Thus, the preferred present antibody exhibits preferably an $EC_{50}$ by this test that is at least better than $10^{-10}$M.

TABLE 1

| Antibody | EC50 to peptide (M) | EC50 to denatured protein (M) |
| --- | --- | --- |
| DSE3 ab1 | 5.65E−11 | 1.09E−07 |
| DSE3 ab90 | 5.43E−11 | 2.22E−10 |
| DSE3 ab94 | 5.79E−11 | 2.20E−10 |
| DSE3 ab116 | 1.66E−10 | 5.52E−07 |
| DSE3 ab119 | 5.25E−11 | 8.90E−08 |
| DSE3 ab120 | 6.55E−11 | 8.80E−11 |
| DSE3 ab166 | 5.24E−11 | 1.73E−10 |

The remaining antibodies showed lower affinity to denatured protein ($10^{-7}$ to $10^{-10}$ M range) than to peptide. All antibodies were also tested by ELISA for binding to captured His-tagged PrP (FIG. 3). None of the antibodies showed binding to captured His-PrP.

All seven antibodies were tested for binding to a panel of eleven tumor cell lines, six implanted primary human tumors, and nine normal cells (Table 2).

TABLE 2

| | Average S/N | | |
| --- | --- | --- | --- |
| Antibody (10 ug/mL) | Tumor Cell Lines (n = 11) | Primary tumors passaged in NOD-SCID mice (n = 6) | Normal Cells (n = 9) |
| DSE3 ab1 | 1.05 | 1.20 | 1.07 |
| DSE3 ab90 | 1.48 | 1.06 | 1.76 |
| DSE3 ab94 | 1.03 | 1.04 | 1.04 |
| DSE3 ab116 | 1.08 | 1.07 | 1.10 |
| DSE3 ab119 | 1.03 | 1.17 | 1.03 |
| DSE3 ab120 | 2.28 | 1.48 | 1.39 |
| DSE3 ab166 | 1.06 | 1.10 | 1.21 |

Figure 4:
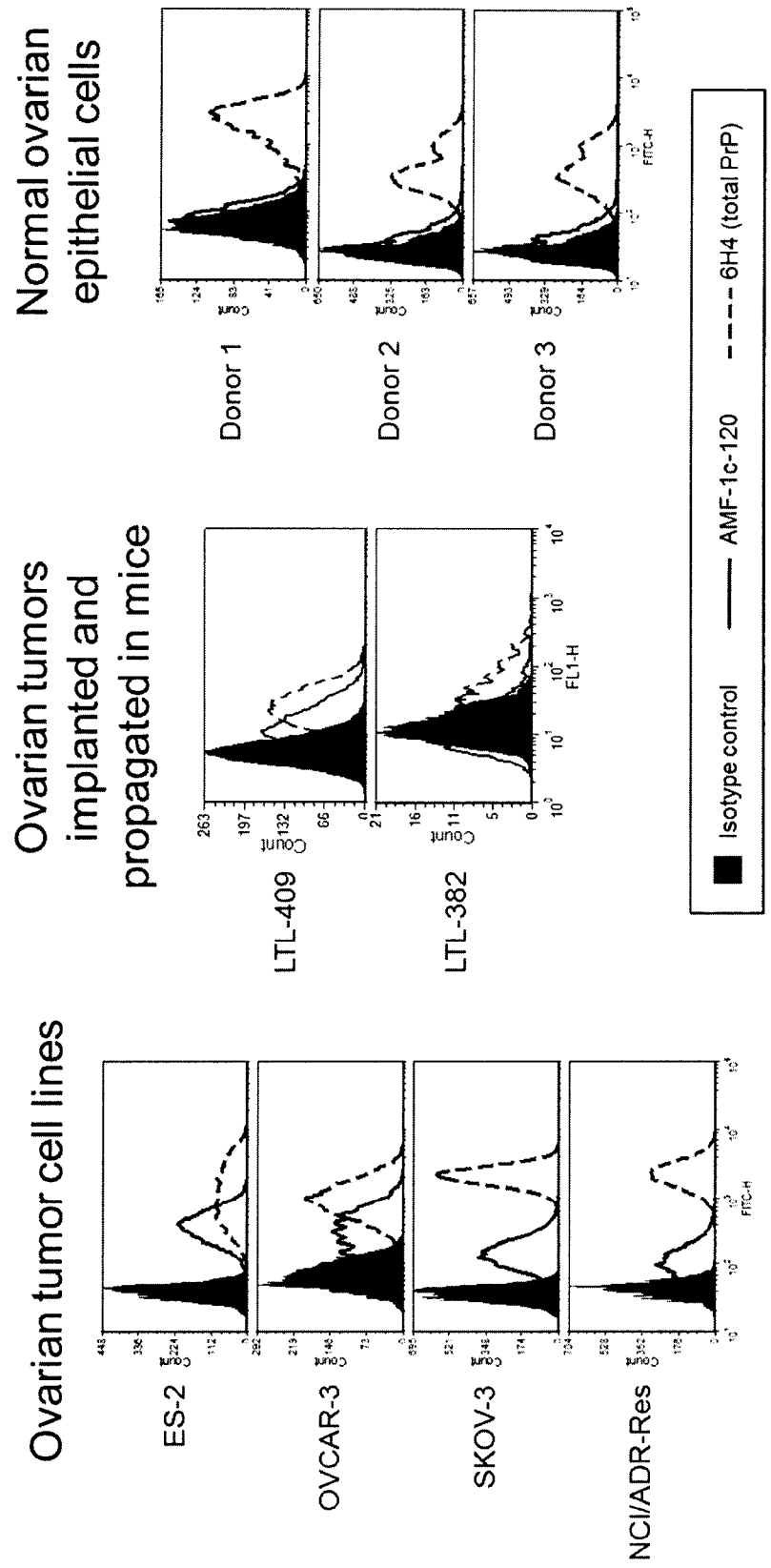

Only two antibodies showed binding to tumor cell lines (DSE3 ab90 and DSE3 ab120). When tested for binding to normal cells, DSE3 ab90 showed more binding to normal cells than to tumor cells. Although DSE3 ab120 also showed a small amount of binding to normal cells, this was less than the amount of binding observed against both tumor cell lines and passaged primary tumors. The binding of DSE ab120 was particularly strong against ovarian tumor cells (FIG. 4), as the antibody bound well to five of six ovarian tumors tested, but did not bind to normal ovarian epithelial cells from three different donors. PrP is expressed on all ovarian cells tested (FIG. 4), although to varying degrees. In order to account for the differences in overall PrP levels, the binding of DSE3 ab120 was normalized to the binding of the control PrP antibody, 6H4 (Table 3).

TABLE 3

| Cell ID | Cell type | Ave S/N with 6H4 control PrP ab (A) | Ave S/N with DSE3 ab120 (B) | Normalized DSE3 ab 120 binding (B − 1)/(A − 1) * 100 |
| --- | --- | --- | --- | --- |
| ES-2 | Ovarian tumor | 52.45 | 4.43 | 10.44 |
| OVCAR-3 | cell line | 10.89 | 2.17 | 11.15 |
| SKOV-3 | | 42.02 | 3.62 | 6.33 |
| NCI/ADR-Res | | 48.89 | 2.57 | 3.13 |
| LTL-409 | Ovarian tumors | 3.51 | 2.79 | 71.56 |
| LTL-382 | implanted and propagated in mice | 1.88 | 1.09 | 9.84 |
| HOEpiC Donor 1 | Normal ovarian epithelium | 8.31 | 1.16 | 2.22 |
| HOEpiC Donor 2 | | 14.17 | 1.27 | 2.02 |
| HOEpiC Donor 3 | | 15.10 | 1.32 | 2.25 |

For the six tumor cells, normalized DSE3 ab120 binding ranged from a low of 3.1 to a high of 71.6 (average=18.8). However, the normalized DSE3 ab120 binding ranged only from 2.0 to 2.3 for the normal ovarian cells.

Figure 5:
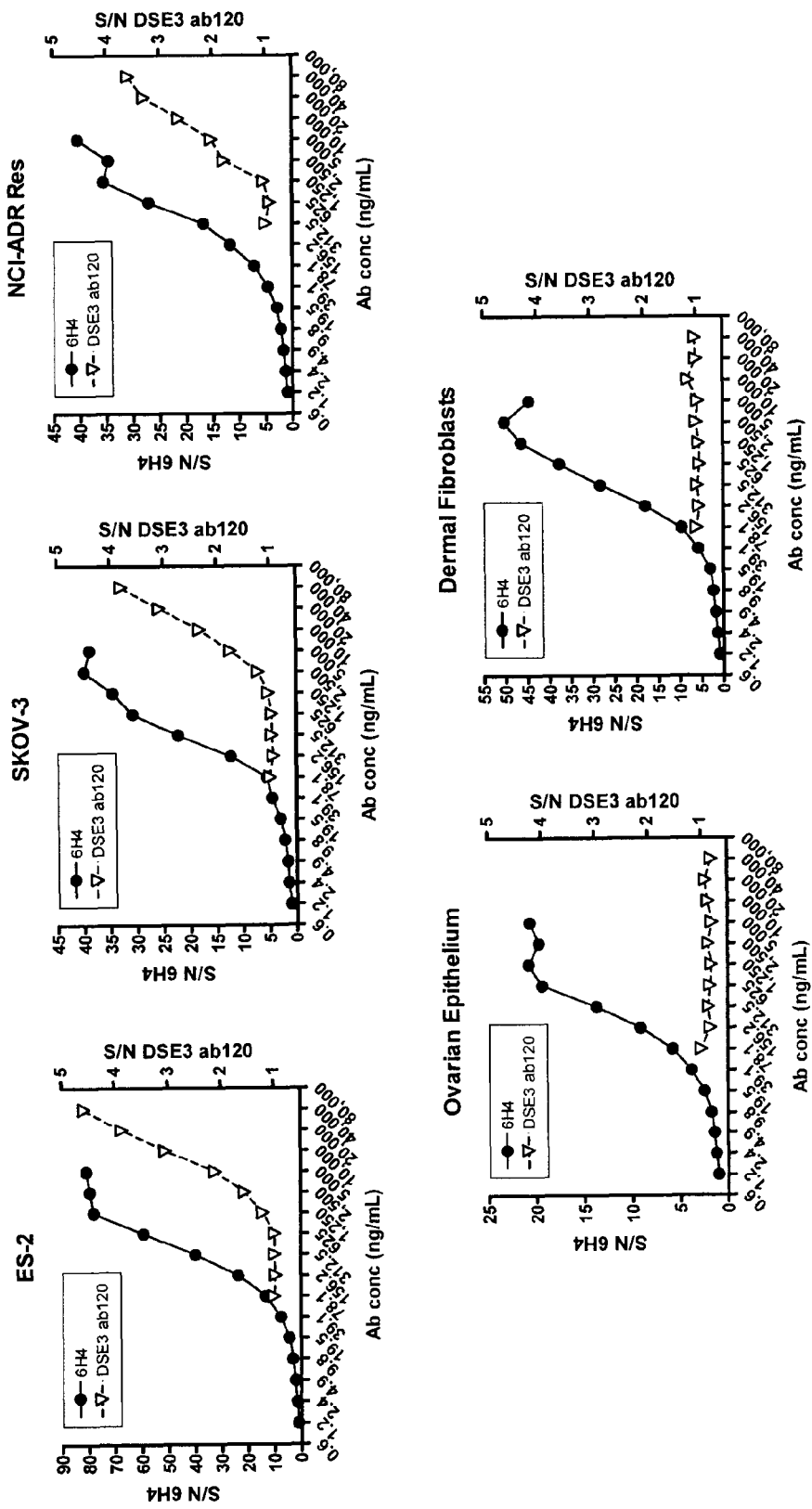

In order to determine the affinity of DSE3 ab120 to tumor cells, antibody titrations were performed on three ovarian tumor cell lines (FIG. 5). Antibody titrations were also performed on two types of normal cells, and confirmed the earlier findings that DSE3 ab120 does not bind to these normal cells. Even though up to 40 ug/mL of antibody was tested, binding saturation was not reached on the tumor cells and affinities could not be determined. In the same experiments, the PrP control antibody 6H4 was also titrated and binding saturation was reached (FIG. 5). For 6H4, the average calculated EC50 is $1.7 \times 10^{-8}$ M and there was no significant difference in the EC50 on tumor and normal cells. Since the binding of DSE3 ab120 to tumor cells is of lower affinity than 6H4, the EC50 for DSE3 ab120 must be lower than $1.7 \times 10^{-8}$ M, and thus at least one log lower than the binding of DSE3 ab120 to denatured PrP ($8.6 \times 10^{-10}$ M).

Figure 6:
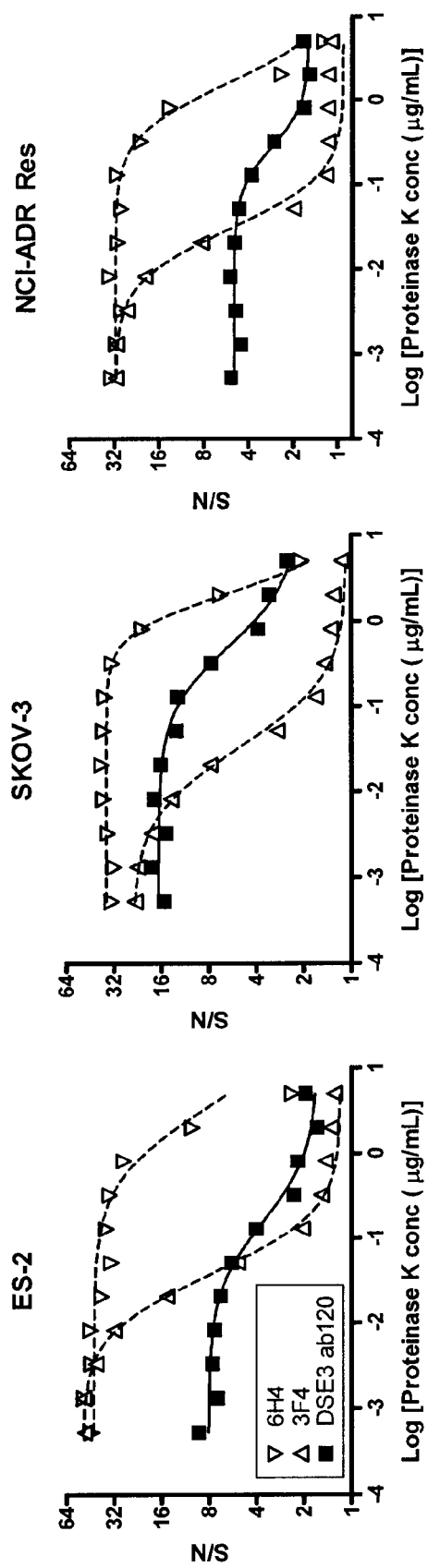

To further investigate the conformation of PrP expressed on the cell surface of ovarian tumor cells, three ovarian tumor cell lines were treated with a range of concentrations of proteinase K (PK) to determine PK sensitivity of the PrP protein expressed by these cells. The natively unfolded N-terminal domain is PK sensitive (FIG. 6, 3F4 epitope). The C-terminal structured domain (α1) is proteinase K-resistant (FIG. 6, 6H4 epitope). The rigid loop (S2-α2) has intermediate PK sensitivity (FIG. 6, DSE3 ab120 epitope), indicating that the rigid loop loses its compact native structure by two criteria: DSE3 ab120 accessibility, and PK sensitivity. The PK EC50 values for each tumor line and epitope were calculated (Table 4).

TABLE 4

| | $EC_{50}$ (mg/mL) (Average of 4 or 5 experiments) | | |
| --- | --- | --- | --- |
| Tumor Line | 3F4 | 6H4 | DSE3 ab120 |
| ES-2 | 0.0121 | 1.1788 | 0.0385 |
| SKOV-3 | 0.0111 | 1.3320 | 0.2157 |
| NCI-ADR Res | 0.0126 | 0.8170 | 0.4380 |
| Average | 0.0119 | 1.1093 | 0.2307 |

Figure 7:
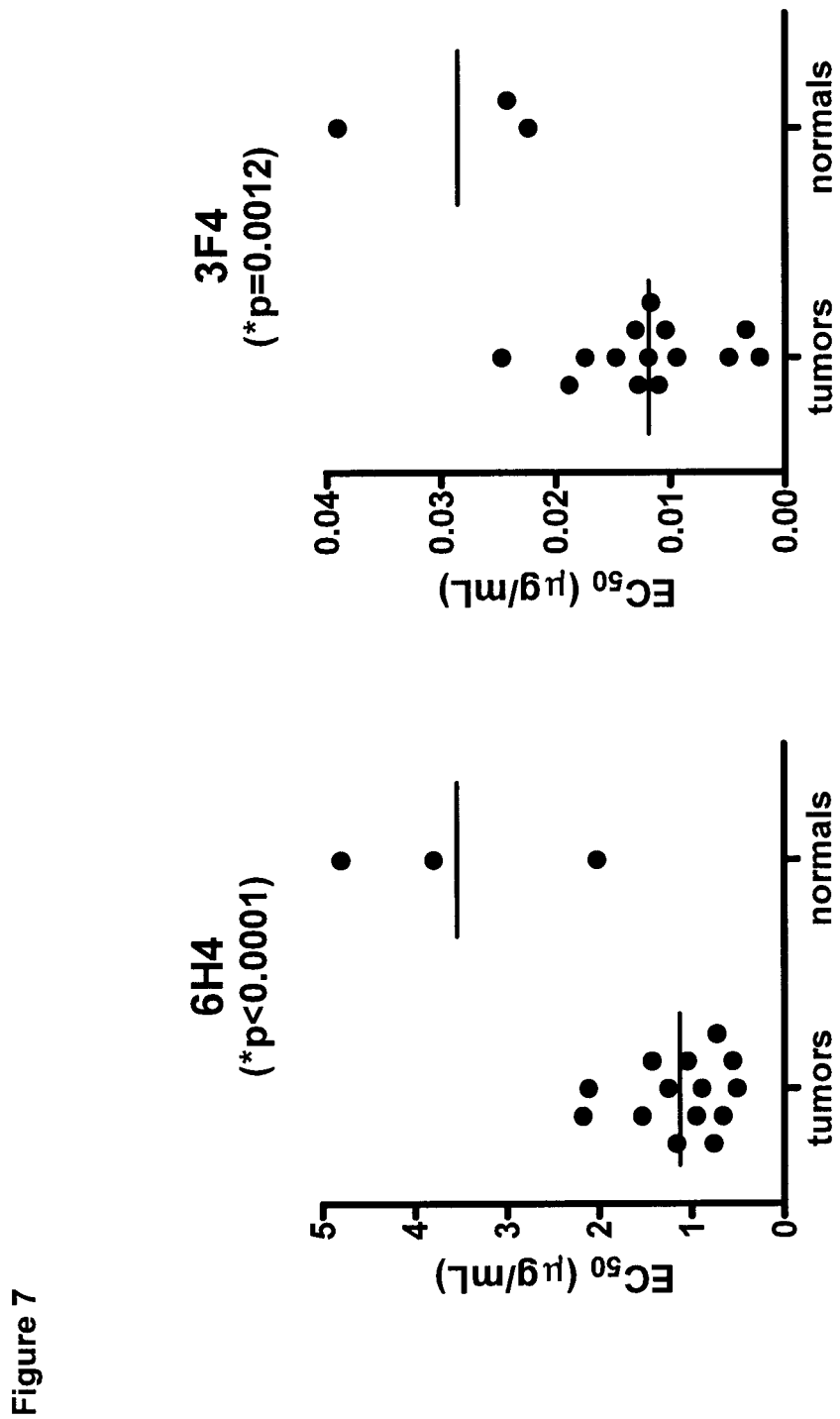
FIG. 7 shows that the PrP presented by ovarian tumour cells is more sensitive to proteinase K digestion than is the PrP presented by normal, ovarian epithelial cells.

PK sensitivity was also evaluated for PrP expressed by normal ovarian cells (FIG. 7). The PK EC50 values are significantly different between tumor and normal cells, indicating that PrP is partially denatured (misfolded) at the surface of ovarian tumor cells compared to normal cells.

Figure 8:
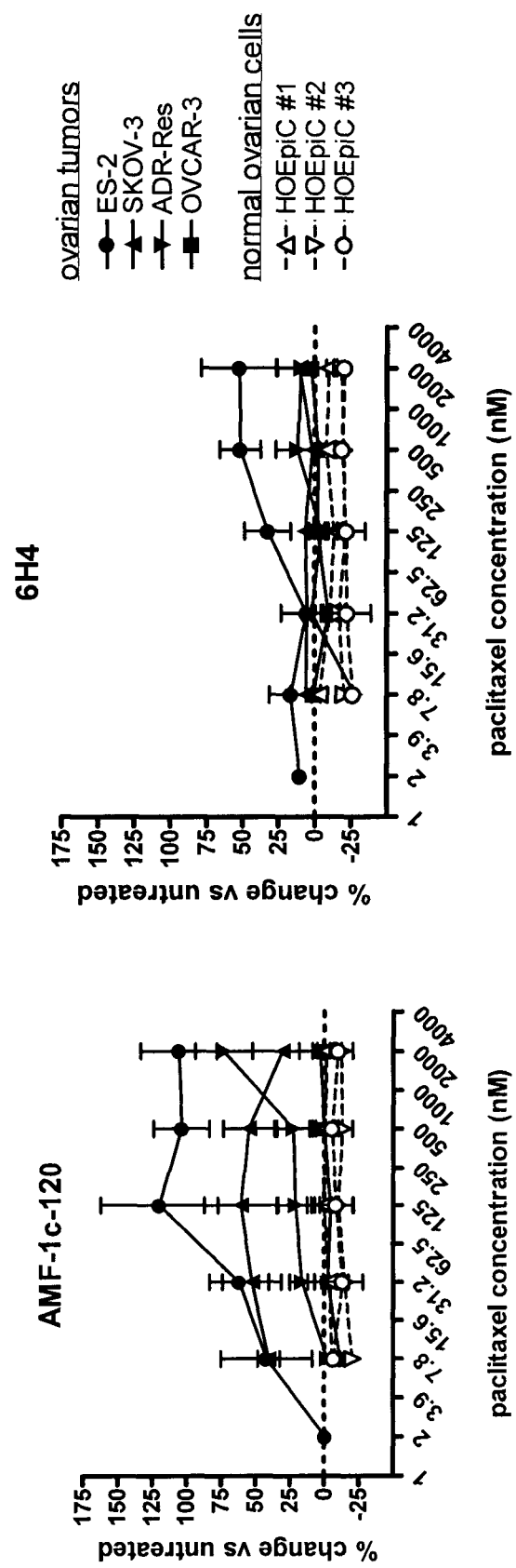
FIG. 8 shows the effect of paclitaxel treatment on antibody binding to normal (dashed lines) and ovarian tumour (solid lines) cells.

The effect of a chemotherapeutic, paclitaxel, on PrP conformation was explored by incubating ovarian cells overnight with increasing concentrations of paclitaxel, followed by detection using DSE3 ab120. As shown in FIG. 8, paclitaxel treatment increases the binding of DSE3 ab120 on the ovarian tumors tested, but not on the three normal ovarian cells obtained from three independent donors. The level of total PrP generally remains constant, as shown by binding of the pan-PrP antibody 6H4, and thus the paclitaxel is inducing structural changes in PrP at the cell surface of ovarian tumors, but not normal cells.

In order to facilitate efficacy in vivo, AMF-1c-120 was conjugated to urease. After conjugation, antibody binding to peptide, denatured PrP, and cells was evaluated (FIGS. 9 and 10) and showed that antibody binding is maintained upon urease conjugation. Activity of the AMF-1c-120/urease in vitro was tested by incubating tumor cell lines with antibody alone, antibody/urease, or urease alone. Although some toxicity was observed with urease alone, considerably more toxicity was mediated by AMF-1c-120/urease. Thus, AMF-1c-120/urease is cytotoxic in vitro.

The efficacy of AMF-1c-120/urease in vivo was tested in the ES-2 xenograft model (FIG. 12), and suggests an effect on tumor growth.

All references cited herein, including all database references and the sequence information referenced therein, and are hereby incorporated herein in their entirety.

We claim:

1. An isolated antibody or fragment thereof that binds to misfolded human prion protein (PrP) epitope MDEYSN-QNN (SEQ ID No. 14), the antibody comprising a heavy chain and a light chain, each chain having a constant region and a variable region, each variable region comprising framework regions and complementarity determining regions (CDRs), wherein the CDRs comprise an amino acid sequence set forth below:

For the heavy chain:

| | | |
|---|---|---|
| CDR1 | TYAMG | (SEQ ID No. 1) |
| CDR2 | VITKSGNTYYASWAKG | (SEQ ID No. 2) |
| CDR3 | YGIGVSYYDI | (SEQ ID No. 3) |

For the light chain:

| | | |
|---|---|---|
| CDR1 | QSSQSLYNKNWLS | (SEQ ID No. 4) |
| CDR2 | KASTLES | (SEQ ID No. 5) |
| CDR3 | QGEFSCSSADCTA | (SEQ ID No. 6). |

2. An antibody or fragment thereof according to claim 1, wherein the light chain variable region comprises SEQ ID No. 7 or 9.

3. An antibody or fragment thereof according to claim 1, wherein the heavy chain variable region comprises SEQ ID No. 8 or 10.

4. An immunoconjugate comprising the antibody or the fragment of claim 1 and a toxin.

5. An immunoconjugate of claim 4, wherein the toxin is urease.

6. An immunoconjugate comprising the antibody or fragment thereof of claim 1 and a detectable label.

7. A pharmaceutical composition comprising an antibody or fragment thereof according to claim 1, or an immunoconjugate comprising said antibody of fragment and a toxin, and a pharmaceutically acceptable carrier.

8. The antibody or fragment thereof according to claim 1, for the treatment of a disorder mediated by misfolded human PrP.

9. The antibody or fragment thereof according to claim 8, for the treatment of cancer or CJD.

10. The antibody or fragment thereof according to claim 9, for the treatment of ovarian cancer or leukemia.

11. The immunoconjugate according to claim 6 for the detection of misfolded PrP.

12. A diagnostic kit comprising an antibody or fragment thereof according to claim 1, and instructions for the use thereof to detect misfolded PrP.

13. A method for detecting misfolded PrP in a biological sample, comprising incubating the sample with an antibody or a fragment thereof according to claim 1, and detecting formation of antibody-bound complex.

14. A method for treating a subject presenting with disease cells having a misfolded PrP phenotype, comprising administering to the subject a pharmaceutical composition according to claim 7 in an amount effective to inhibit the growth or proliferation of said disease cells.

15. The method according to claim 14, wherein the disease cells are cancer cells, optionally leukemia cells or ovarian cancer cells.

16. The method according to claim 15, wherein the subject is also treated with paclitaxel.

17. A method for treating a subject presenting with a disease in which PrP aggregation is implicated, comprising administering to the subject a pharmaceutical composition according to claim 7 in an amount effective to inhibit the progression of PrP aggregation.

18. The method according to claim 17, wherein the disease is a transmissible spongiform encephalopathy, optionally wherein the disease is CJD.

* * * * *